(12) United States Patent
Ohrui et al.

(10) Patent No.: US 8,431,244 B2
(45) Date of Patent: Apr. 30, 2013

(54) INDENOCHRYSENE DERIVATIVE AND ORGANIC LIGHT-EMITTING DEVICE USING SAME

(75) Inventors: Hiroki Ohrui, Kawasaki (JP); Akihito Saitoh, Yokohama (JP); Chika Negishi, Yokosuka (JP); Hironobu Iwawaki, Yokohama (JP); Masanori Muratsubaki, Hachioji (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 426 days.

(21) Appl. No.: 12/594,023

(22) PCT Filed: May 16, 2008

(86) PCT No.: PCT/JP2008/059494
§ 371 (c)(1),
(2), (4) Date: Sep. 30, 2009

(87) PCT Pub. No.: WO2008/146720
PCT Pub. Date: Dec. 4, 2008

(65) Prior Publication Data
US 2010/0127618 A1 May 27, 2010

(30) Foreign Application Priority Data
May 28, 2007 (JP) .................... 2007-140749

(51) Int. Cl.
*H01L 51/54* (2006.01)
*C09K 11/06* (2006.01)

(52) U.S. Cl.
USPC ........... 428/690; 428/917; 313/502; 313/504; 257/40; 585/27

(58) Field of Classification Search .................... None
See application file for complete search history.

(56) References Cited

U.S. PATENT DOCUMENTS

| | | | |
|---|---|---|---|
| 7,101,632 B2 | 9/2006 | Igarashi | 428/690 |
| 2001/0008711 A1 | 7/2001 | Igarashi | 428/690 |
| 2004/0076853 A1 | 4/2004 | Jarikov | 428/690 |
| 2004/0222737 A1* | 11/2004 | Raychaudhuri et al. | 313/504 |
| 2006/0210830 A1 | 9/2006 | Funahashi et al. | 428/690 |
| 2007/0249878 A1 | 10/2007 | Iwawaki et al. | 585/27 |
| 2007/0252141 A1 | 11/2007 | Negishi et al. | 257/440 |
| 2008/0286611 A1 | 11/2008 | Muratsubaki et al. | 428/704 |
| 2009/0033210 A1 | 2/2009 | Saitoh et al. | 313/504 |
| 2009/0121625 A1 | 5/2009 | Ohrui et al. | 313/504 |
| 2009/0278118 A1 | 11/2009 | Ohrui et al. | 257/40 |
| 2009/0278447 A1 | 11/2009 | Saitoh et al. | 313/504 |

FOREIGN PATENT DOCUMENTS

| | | |
|---|---|---|
| EP | 1690912 A1 * | 8/2006 |
| JP | 10-189247 | 7/1998 |
| JP | 10-294177 | 11/1998 |
| JP | 2001-192652 | 7/2001 |
| JP | 2004043349 A * | 2/2004 |
| JP | 3731971 B2 | 1/2006 |
| JP | 2006-052323 | 2/2006 |
| JP | 2006-256979 | 9/2006 |

OTHER PUBLICATIONS

Tucker et al. "Spectroscopic Properties of Polycyclic Aromatic Hydrocarbons: Effect of Solvent Polarity on Fluorescence Emission Behavior of Select Fluoranthene, Fluorenochrysene, Indenochrysene, and Indenopyrene Derivatives" Applied Spectroscopy 1991, 45, 1699-1705. Year of publication: 1991.*
Machine translation of JP2004-043349. Date of publication: Feb. 12, 2004.*
Murov, Steven L., et al. "Handbook of Photochemistry" 1993 (10 pages).
Cho, Bongsup P. et al., "Polycyclic Flouranthene Hydrocarbons. 2. A New General Synthesis" J. Org. Chem. vol. 52, pp. 5668-5678, 1987.
Minabe, Mashiro et al., "Electrophilic Substitution of Polycyclic Fluoranthene Hydrocarbons" American Chemical Society, 1989 (4 pages).
Cho, Bongsup P. et al., "Attempted Synthesis of Fjord-region Containing Polycyclic Fluoranthenes reveals a steric-Driven Double Wagner-Meerwein Rearrangement" vol. 37, No. 10 pp. 1535-1538, 1996.
International Preliminary Report on Patentability in PCT/JP2008/059494 dated Dec. 10, 2009—5 pages.

* cited by examiner

*Primary Examiner* — Jennifer A Chriss
*Assistant Examiner* — Andrew K Bohaty
(74) *Attorney, Agent, or Firm* — Fitzpatrick, Cella, Harper, Scinto

(57) ABSTRACT

There is provided an organic light-emitting device having an optical output with a high efficiency, a high luminance, and a long life. The organic light-emitting device includes an anode, a cathode, and a layer including an organic compound interposed between the anode and the cathode, in which either one of the anode and the cathode is formed of a transparent or translucent electrode material, and in which the layer includes at least one indenochrysene derivative represented by the general formula (1):

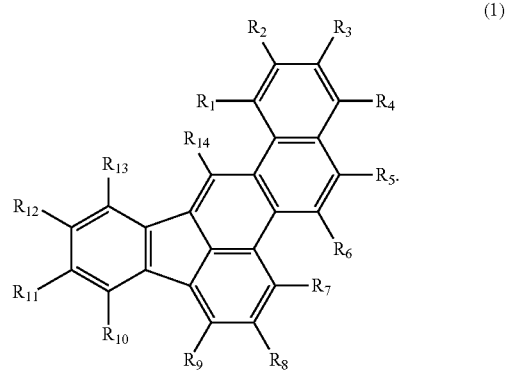

8 Claims, 5 Drawing Sheets

INDENOCHRYSENE DERIVATIVE AND ORGANIC LIGHT-EMITTING DEVICE USING SAME

TECHNICAL FIELD

The present invention relates to an indenochrysene derivative and an organic light-emitting device using the derivative.

BACKGROUND ART

An organic light-emitting device is a device having a thin film which contains a fluorescent or phosphorescent organic compound and is interposed between electrodes. Electrons and holes (positive holes) are injected from the respective electrodes, whereby excitons of the fluorescent or phosphorescent compound are produced. The excitons radiate light upon return thereof to a ground state. Recent progress of an organic light-emitting device is remarkable, and the characteristics of the device enable a thin and light weight light-emitting device with a high luminance at a low applied voltage, a variety of emission wavelengths, and a high-speed responsibility. From this fact, it is suggested that the device have potential to find use in a wide variety of applications.

However, in the present circumstances, an optical output with a higher luminance or a higher conversion efficiency is needed. In addition, the organic light-emitting device still involves a large number of problems in terms of durability such as a change over time due to long-term use and degradation due to an atmospheric gas containing oxygen, moisture or the like. Further, when the application of the device to a full-color display or the like is taken into consideration, the emission of blue, green, or red light with good color purity is needed. However, these problems have not been sufficiently solved yet.

The use of a fused ring aromatic compound as a component for an organic light-emitting device has been proposed as a method of solving the above-mentioned problems. For example, in each of Japanese Patent Application Laid-Open No. 2006-256979, Japanese Patent Application Laid-Open No. 2006-52323, US Published Application No. 2004/0076853, U.S. Pat. No. 7,101,632, and Japanese Patent Application Laid-Open No. 2001-192652, a fused ring aromatic compound is used as a component for an organic light-emitting device. For example, Japanese Patent Application Laid-Open No. 2006-256979 discloses, as a light-emitting material, a chrysene derivative obtained by substitution at the 5- and 6-positions of a chrysene skeleton with an arylamine. Japanese Patent Application Laid-Open No. 2006-52323 discloses a dimer of chrysene as a light-emitting material. In addition, US Published Application No. 2004/0076853 discloses that unsubstituted has a large intermolecular interaction and is unsuitable for use in a light-emitting material, but easily associates and is therefore suitable for use as a second host. In addition, U.S. Pat. No. 7,101,632 and Japanese Patent Application Laid-Open No. 2001-192652 each disclose a triarylamine having a fused polycyclic group as a light-emitting material, and each disclose, as an example of the fused polycyclic group, an indenochrysene skeleton. In addition, Japanese Patent No. 3,731,971 discloses an organic light-emitting device using a naphthofluoranthene derivative, which is a constitutional isomer of the indenochrysene skeleton, as a component.

DISCLOSURE OF THE INVENTION

The present invention has been accomplished with a view to solving the above-mentioned problems of the related art.

An object of the present invention is to provide a novel indenochrysene derivative and an organic light-emitting device using the indenochrysene derivative. Another object of the present invention is to provide an organic light-emitting device that can be easily produced at a relatively low cost.

The present inventors have conducted extensive studies with a view to solving the above-mentioned problems, and thus completed the present invention. That is, an indenochrysene derivative of the present invention is represented by the following General Formula (1):

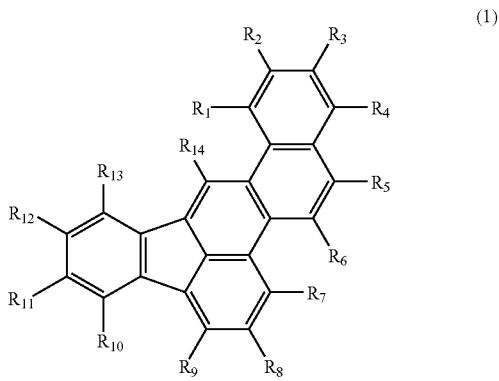

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ each represent, independently of one another, a substituent selected from the group consisting of a hydrogen atom, a substituted or unsubstituted alkyl group, a substituted or unsubstituted alkenyl group, a substituted or unsubstituted alkynyl group, an aryl group having a substituent constituted of a hydrocarbon or a substituent having an unsaturated bond and containing a hetero atom, an unsubstituted aryl group, a substituted or unsubstituted heterocyclic group, a substituted or unsubstituted fused polycyclic aromatic group, and a substituted or unsubstituted fused heteropolycyclic group, provided that any one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ represents a substituent selected from an aryl group having a substituent constituted of a hydrocarbon or a substituent having an unsaturated bond and containing a hetero atom, an unsubstituted aryl group, a substituted or unsubstituted heterocyclic group, a substituted or unsubstituted fused polycyclic aromatic group, and a substituted or unsubstituted fused heteropolycyclic group.

The indenochrysene derivative of the present invention has less intermolecular interaction, and has a high quantum yield. As a result, according to the present invention, there can be provided an organic light-emitting device having an optical output with a high efficiency and a high luminance, and showing high durability.

Further features of the present invention will become apparent from the following description of exemplary embodiments with reference to the attached drawings.

BEST MODE FOR CARRYING OUT THE INVENTION

Figure 1:
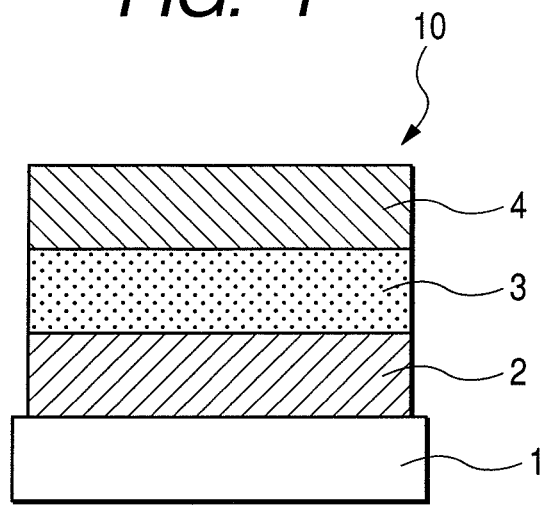
FIG. 1 is a cross sectional view illustrating an organic light-emitting device according to a first embodiment of the present invention.

Hereinafter, the present invention will be described in detail.

First, the indenochrysene derivative of the present invention will be described.

The indenochrysene derivative of the present invention is represented by General Formula (1).

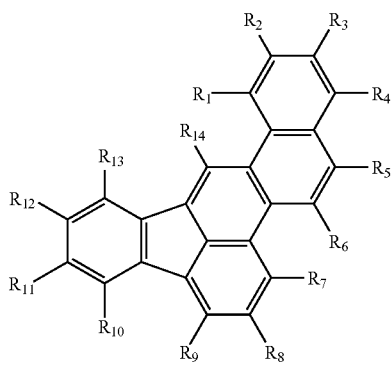

(1)

In General Formula (1), $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ each represent, independently of one another, a substituent selected from the group consisting of a hydrogen atom, a substituted or unsubstituted alkyl group, a substituted or unsubstituted alkenyl group, a substituted or unsubstituted alkynyl group, an aryl group having a substituent constituted of a hydrocarbon or a substituent having an unsaturated bond and containing a hetero atom, an unsubstituted aryl group, a substituted or unsubstituted heterocyclic group, a substituted or unsubstituted fused polycyclic aromatic group, and a substituted or unsubstituted fused heteropolycyclic group.

However, in the present invention, any one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ represents a substituent selected from an aryl group having a substituent constituted of a hydrocarbon or a substituent having an unsaturated bond and containing a hetero atom, an unsubstituted aryl group, a substituted or unsubstituted heterocyclic group, a substituted or unsubstituted fused polycyclic aromatic group, and a substituted or unsubstituted fused heteropolycyclic group.

Examples of the alkyl group represented by $R_1$ to $R_{14}$ include, but of course not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, an adamantyl group, a benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of the alkenyl group represented by $R_1$ to $R_{14}$ include, but of course not limited to, a vinyl group, a 1-propenyl group, a 2-propenyl group, a 1-butenyl group, a 2-butenyl group, and a 3-butenyl group.

Examples of the alkynyl group represented by $R_1$ to $R_{14}$ include, but of course not limited to, an ethynyl group, a 1-propynyl group, a 2-propynyl group, a 1-butynyl group, a 2-butynyl group, and a 3-butynyl group.

Examples of the aryl group represented by any one of $R_1$ to $R_{14}$ include, but of course not limited to, a phenyl group, a 4-methylphenyl group, a 4-ethylphenyl group, a 3,5-dimethylphenyl group, a 2,6-diethylphenyl group, a mesityl group, a 4-tert-butylphenyl group, a biphenyl group, and a 4-pyridylphenyl group. The above-mentioned aryl group particularly preferably has a substituent constituted of a hydrocarbon or a substituent having an unsaturated bond and containing a hetero atom. The term "substituent constituted of a hydrocarbon" as herein employed refers to a substituent such as an alkyl group such as a methyl group, an ethyl group, or a tert-butyl group; or an aryl group such as a phenyl group. In addition, the term "substituent having an unsaturated bond and containing a hetero atom" herein employed refers to a heterocyclic group such as a pyridyl group.

Examples of the heterocyclic group represented by $R_1$ to $R_{14}$ include, but of course not limited to, a pyridyl group, a pyrrolyl group, a bipyridyl group, a methylpyridyl group, a pyrimidinyl group, a pyrazinyl group, a pyridazinyl group, a terpyrrolyl group, a thienyl group, a terthienyl group, a propylthienyl group, a furyl group, an oxazolyl group, an oxadiazolyl group, a thiazolyl group, and a thiadiazolyl group.

Examples of the fused polycyclic aromatic group represented by $R_1$ to $R_{14}$ include, but of course not limited to, a naphthyl group, an acenaphthyrenyl group, an anthryl group, a phenanthryl group, a pyrenyl group, an acephenanthrenyl group, an aceanthrylenyl group, a chrysenyl group, a dibenzochrysenyl group, a benzoanthryl group, a dibenzoanthryl group, a naphthacenyl group, a picenyl group, a pentacenyl group, a fluorenyl group, a 9,9-dihydroanthryl group, a triphenylenyl group, a perylenyl group, a fluoranthenyl group, a benzofluoranthenyl group, and a benzophenanthryl group.

Examples of the fused hetelopolycyclic group represented by $R_1$ to $R_{14}$ include, of course not limited to, a quinolyl group, an isoquinolyl group, a benzothienyl group, a dibenzothienyl group, a benzofuryl group, an isobenzofuryl group, a dibenzofuryl group, a quinoxalinyl group, a naphthridinyl group, a quinazolinyl group, a phenantridinyl group, an indolidinyl group, a phenadinyl group, a carbazolyl group, an acridinyl group, a phenadinyl group, a diazafluorenyl group, an azafluorenyl group, an azafluoranthenyl group, and an azabenzofluoranthenyl group.

Examples of the substituent that the above-mentioned alkyl group, alkenyl group, alkynyl group, aryl group, fused heteropolycyclic group, fused polycyclic aromatic group, and heterocyclic group may further have include, of course not limited to, alkyl groups such as a methyl group, an ethyl group, a propyl group, and a tert-butyl group; aryl groups such as a phenyl group and a biphenyl group; heterocyclic groups such as a thienyl group, a pyrrolyl group, and a pyridyl group; a 9,9-dimethyl-9H-fluorenyl group; 9,9,9',9'-tetramethyl-9H-9H'-2,2'-bifluorenyl group; a cyano group; and a nitro group.

As another embodiment of the indenochrysene derivative of the present invention, indenochrysene represented by the following General Formula (2) is mentioned.

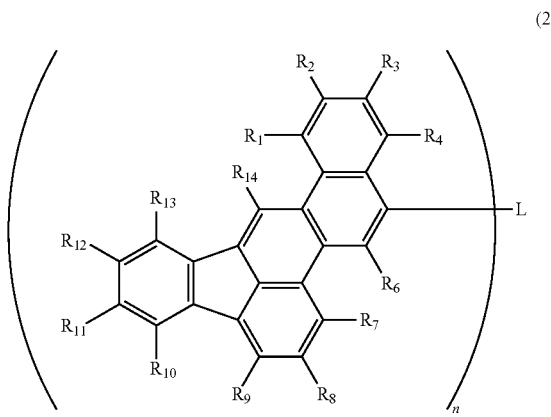

(2)

In General Formula (2), n represents an integer of 2 to 4.

In General Formula (2), L represents a single bond, or an n-valent linking group derived from any one of a substituted or unsubstituted alkane, a substituted or unsubstituted alkene, alkyne, an aromatic ring having a substituent constituted of a hydrocarbon or a substituent having an unsaturated bond and containing a hetero atom, an unsubstituted aromatic ring, a substituted or unsubstituted heterocyclic ring, a substituted or unsubstituted fused polycyclic aromatic ring, and a substituted or unsubstituted fused heteropolycyclic ring.

Examples of the linking group derived from alkane represented by L include, but of course not limited to, an ethylene group, a propylene group, and a butylene group.

Examples of the linking group derived from alkene represented by L include, but of course not limited to, a vinylene group, a propynylene group, and a butynylene group.

Examples of the linking group derived from an aromatic ring represented by L include, but not limited to, a phenylene group and a biphenylene group.

Examples of the linking group derived from a heterocyclic ring represented by L include, but not limited to, a pyridinylene group and a bipyridinylene group.

Examples of the linking group derived from a fused polycyclic aromatic ring represented by L include, but not limited to, a fluorenylene group, a bifluorenylene group, a naphthylene group, an anthrylene group, and a chrysenylene group.

Examples of the linking group derived from a fused heteropolycyclic ring represented by L include, but not limited to, an azafluorenylene group, a diazafluorenylene group, and a naphthylidinylene group.

Examples of the substituent which the above-mentioned linking group may have include, for example, but of course not limited to, an alkyl group such as a methyl group, an ethyl group, a propyl group, or a tert-butyl group, an aryl group such as a phenyl group or a biphenyl group, a heterocyclic group such as a thienyl group or a pyrrolyl group, a cyano group, or a nitro group. The above-mentioned aromatic ring particularly preferably has a substituent constituted of a hydrocarbon or a substituent having an unsaturated bond and containing a hetero atom. The term "substituent constituted of a hydrocarbon" as herein employed refers to a substituent such as an alkyl group such as a methyl group, an ethyl group, or a tert-butyl group; or an aryl group such as a phenyl group. In addition, the term "substituent having an unsaturated bond and containing a hetero atom" herein employed refers to a heterocyclic group such as a pyridyl group.

In General Formula (2), $R_1$ to $R_4$ and $R_6$ to $R_{14}$ each represent, independently of one another, a substituent selected from a hydrogen atom, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused heteropolycyclic group.

Specific examples of each of the alkyl group, the alkenyl group, the alkynyl group, the aryl group, the heterocyclic group, the fused heteropolycyclic group, and the fused polycyclic aromatic group defined above are the same as those mentioned above for $R_1$ to $R_{14}$ in General Formula (1). Specific examples of the substituent which each of the alkyl group, the alkenyl group, the alkynyl group, the aryl group, the heterocyclic group, the fused heteropolycyclic group, and the fused polycyclic aromatic group described above may have are also the same as those mentioned above for $R_1$ to $R_{14}$ in General Formula (1).

$R_1$ to $R_4$ and $R_6$ to $R_{14}$ may be identical to or different from one another. In addition, substituents of the same kind possessed by different indenochrysene skeletons may be identical to or different from each other. That is, substituents having the same number out of $R_1$'s to $R_4$'s and $R_6$'s to $R_{14}$'s in the respective indenochrysene skeletons shown in General Formula (2) may be identical to or different from each other.

The indenochrysene derivative of the present invention can be used as a material for an organic light-emitting device. In particular, the derivative can be used as a material for constituting a light-emitting layer. The use of the indenochrysene derivative of the present invention as a material constituting a light-emitting layer improves the emission efficiency of the device, allows the device to maintain a high luminance for a long period of time, and suppresses energization degradation of the device.

Meanwhile, molecular orbital calculation for a compound obtained by substitution at the 5-position of an indenochrysene skeleton with benzo[k]fluoranthene suggests the following. That is, it is suggested that a LUMO expands onto an acenaphthylene moiety of benzo[k]fluoranthene with the indenochrysene skeleton being a center. On the other hand, it is suggested that a HOMO expands onto a naphthalene moiety including a position of bonding to indenochrysene with the benzo[k]fluoranthene skeleton being a center. Accordingly, in the compound, the LUMO expands from the indenochrysene skeleton toward the benzo[k]fluoranthene skeleton, whereby the electron-trapping property is improved, and the emission color is improved. The above-mentioned effect of the expansion of the LUMO and the HOMO similarly develops also when a fused polycyclic aromatic group such as a naphthyl group, an acenaphthylenyl group, a phenanthryl group, a pyrenyl group, an acephenanthrylenyl group, a naphthacenyl group, a picenyl group, a pentacenyl group, a fluorenyl group, a triphenylenyl group, a perylenyl group, a benzofluoranthenyl group, or a benzophenanthryl group is introduced into the 5-position of the indenochrysene skeleton.

On the other hand, in the indenochrysene derivative of the present invention, by introducing a substituent which increases the emission quantum yield into the indenochrysene skeleton, the quantum yield of the entirety molecule is improved.

Meanwhile, according to Steaven L. Murov, Ian Carmichael, Gordon L. Hug, Handbook of Photochemistry, 1993, the fluorescent quantum yields of various compounds including unsubstituted indenochrysene are as shown in Table 1 below. Incidentally, the value for the unsubstituted indenochrysene is an experimental value determined by comparison with a value for diphenylanthracene being defined as 0.95.

TABLE 1

| Compound | Quantum yield |
| --- | --- |
| Indenochrysene | 0.39 |
| p-terphenyl | 0.77 |
| Fluorene | 0.68 |
| Fluoranthene | 0.35 |
| Benzo[k]fluoranthene | 1.0 |
| Pyrene | 0.65 |
| Perylene | 0.75 |
| Benzene | 0.06 |
| Biphenyl | 0.15 |
| Triphenylamine | 0.045 |

As shown in Table 1, the quantum yield of each of p-terphenyl, fluorene, benzo[k]fluoranthene, pyrene, and perylene exceeds that of the unsubstituted indenochrysene. Accordingly, the introduction of any one of those substituents into an indenochrysene skeleton further improves the quantum yield of fluorescence.

As described above, the introduction of a skeleton having a higher quantum yield than that of unsubstituted indenochrysene as a substituent into an indenochrysene skeleton improves the emission efficiency of the unsubstituted indenochrysene so that the unsubstituted indenochrysene serves as a particularly excellent light-emitting material.

In addition, the 5-position of an indenochrysene skeleton has a high reactivity. Accordingly, when a substituent is introduced into the 5-position, the chemical stability of the skeleton can further be improved, which is preferable. Further, when a skeleton having a high quantum yield of fluorescence is introduced as a substituent into the 5-position, not only the improvement in chemical stability but also significant improvement in quantum yield of fluorescence can be attained, which is particularly preferable.

Meanwhile, in an indenochrysene derivative which is a compound obtained by substitution at the 5-position of an indenochrysene skeleton and is represented by General Formula (2), the introduction of the linking group L including a fused polycyclic aromatic group or a fused heteropolycyclic group can exert an effect on steric hindrance and rotational barrier due to peri-position. As a result, not only the chemical stability of the compound itself but also the fluorescent quantum yield of the entire molecule of the indenochrysene derivative can be improved.

On the other hand, since benzene, biphenyl, and triphenylamine each have a lower quantum yield than that of an unsubstituted indenochrysene derivative, the introduction of those substituents into an indenochrysene skeleton cannot be said to improve the quantum yield of fluorescence.

In particular, as a substituent to be introduced into an indenochrysene skeleton, triphenylamine as one of the tertiary amines has an extremely low fluorescent quantum yield, and the substituent itself is unstable against oxygen. Therefore, the use thereof as a substituent is inappropriate.

Incidentally, although benzene and biphenyl each have a lower quantum yield than that of an unsubstituted indenochrysene derivative, they may be introduced as the linking group L of the indenochrysene derivative represented by General Formula (2). This is because the introduction of benzene or biphenyl as the linking group L results in bonding of two or more indenochrysene skeleton moieties through the linking group so that the quantum yield is markedly improved as compared to that of a single indenochrysene.

Specific structural formulae of the indenochrysene derivatives of the present invention are shown below. However, they are merely typical examples of the indenochrysene derivatives of the present invention, and the present invention is not limited thereto.

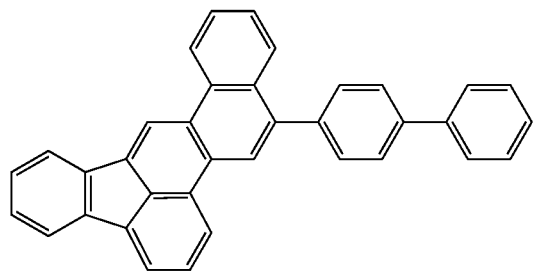

101

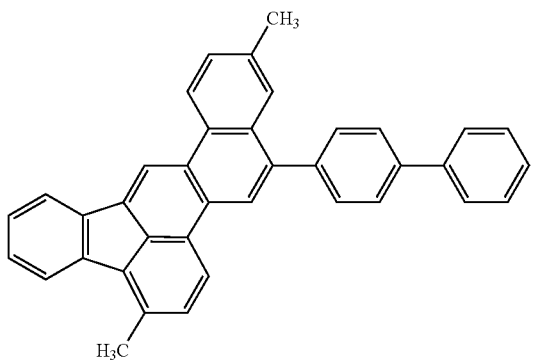

102

-continued
103
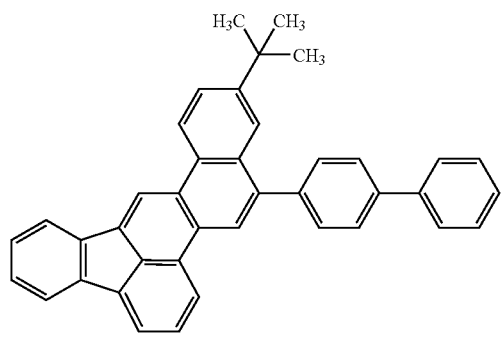
104
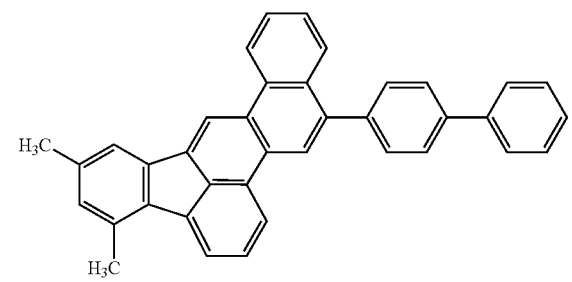
105
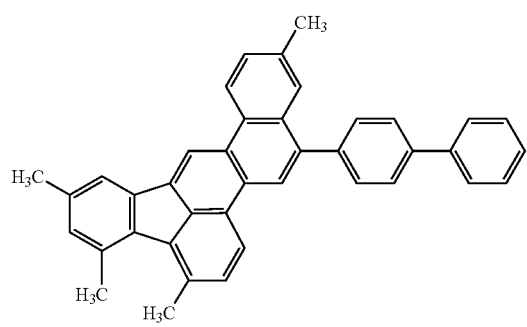
106
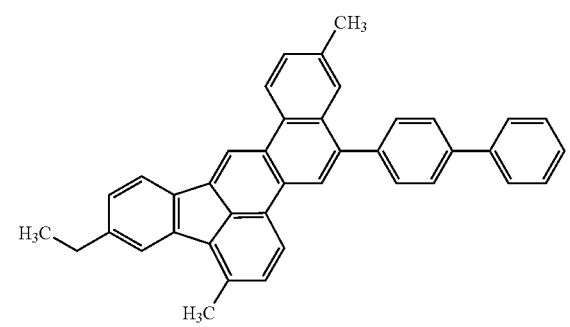
107
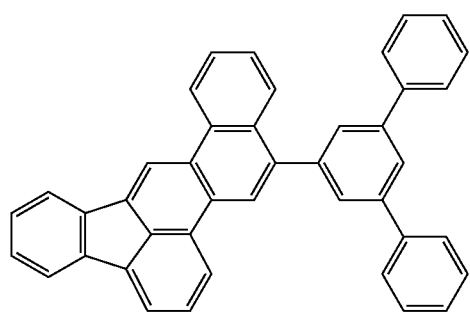
108
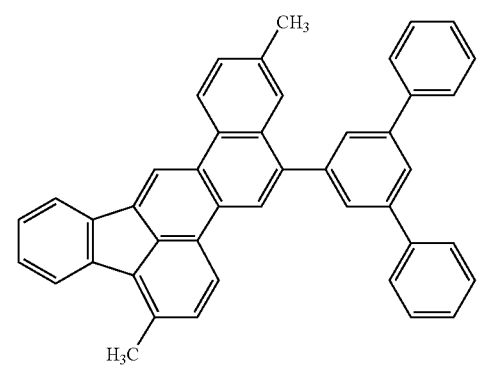
109
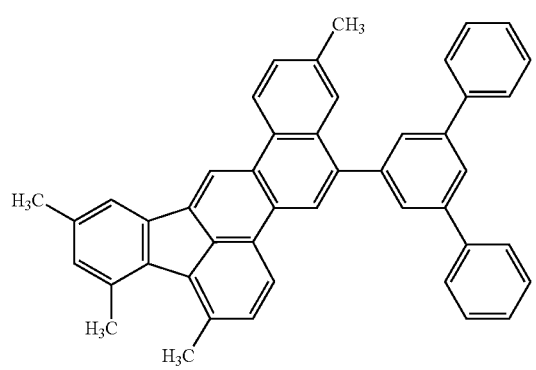
110
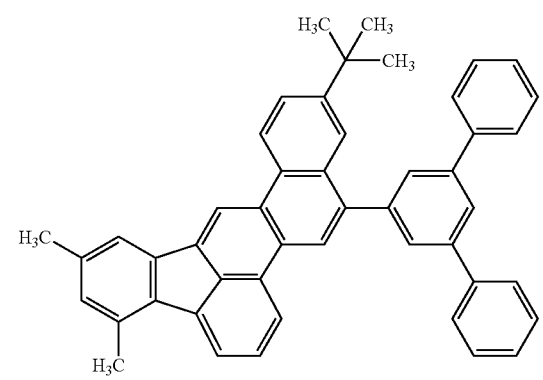

-continued
111
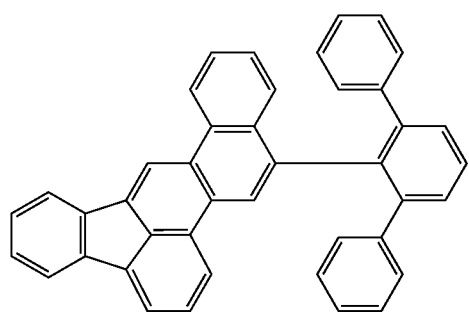
112
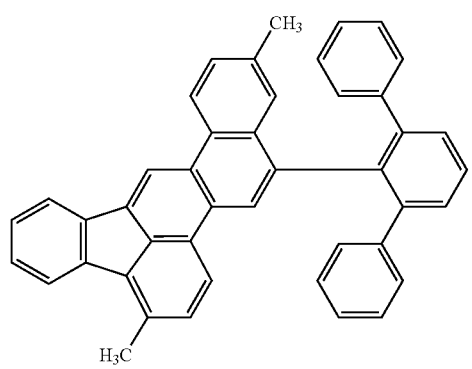
113
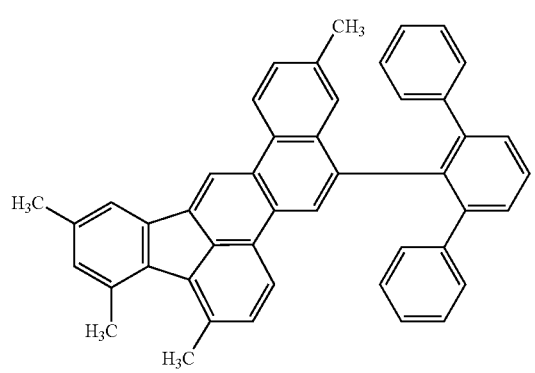
114
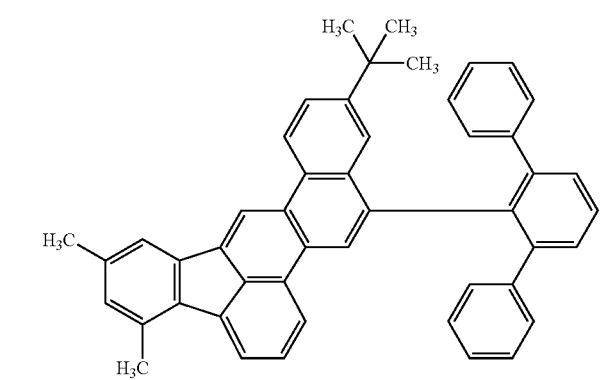
201
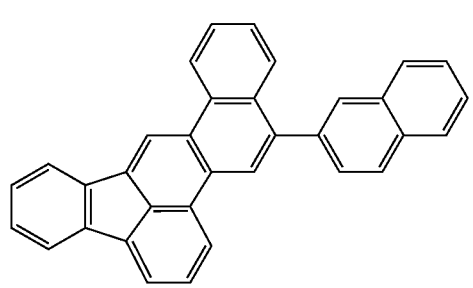
202
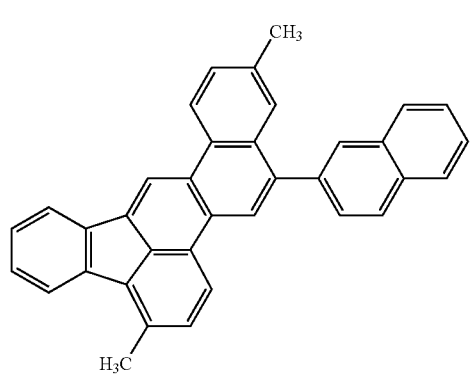
203
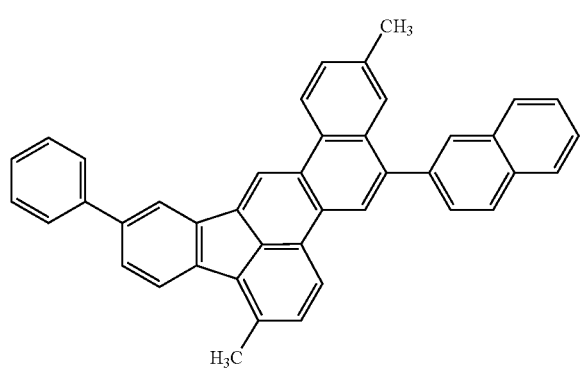
204
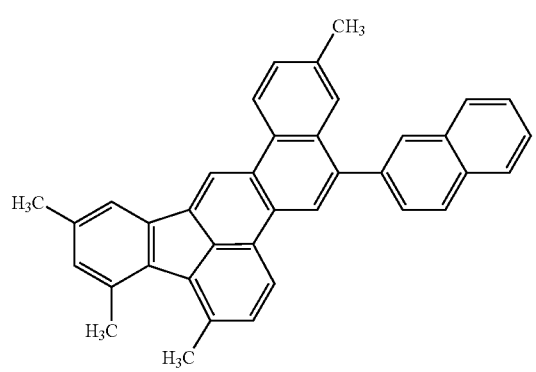

-continued
205
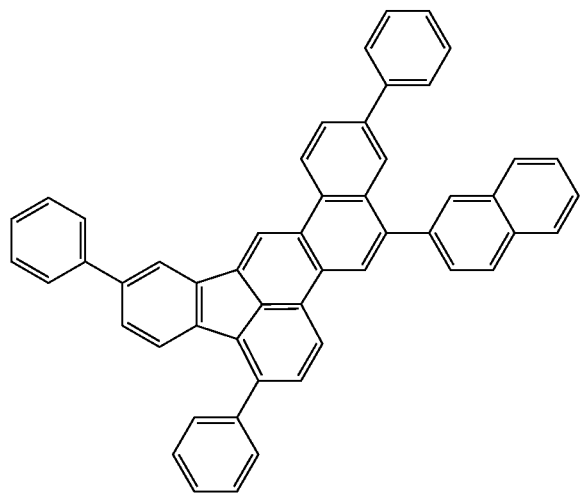
206
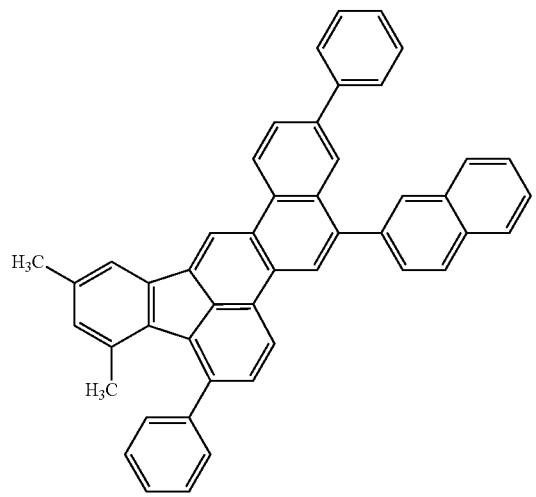
207
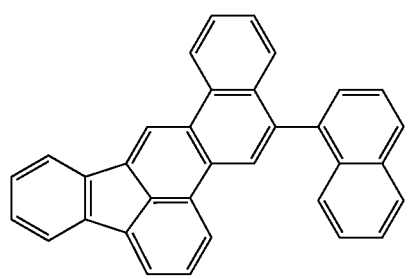
208
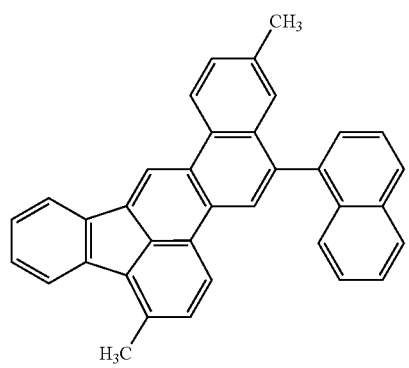
209
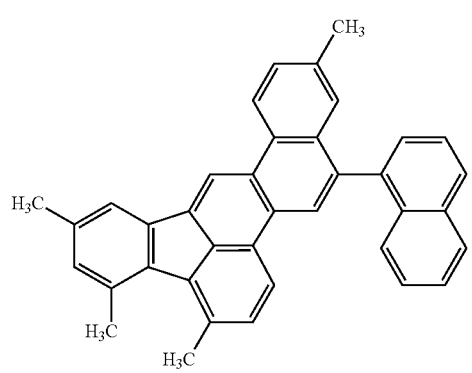
210
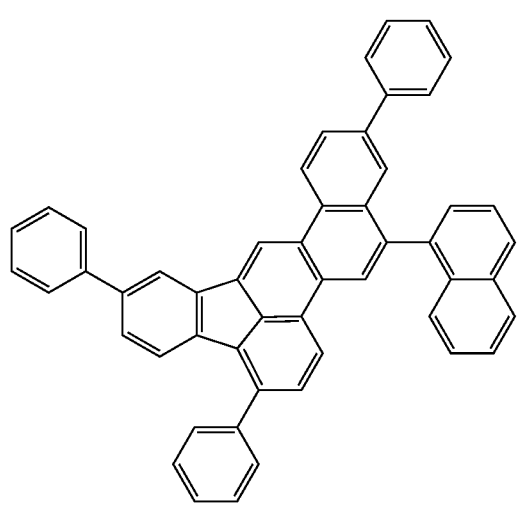

-continued
211
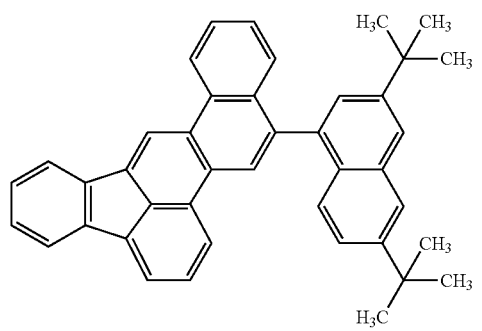
212
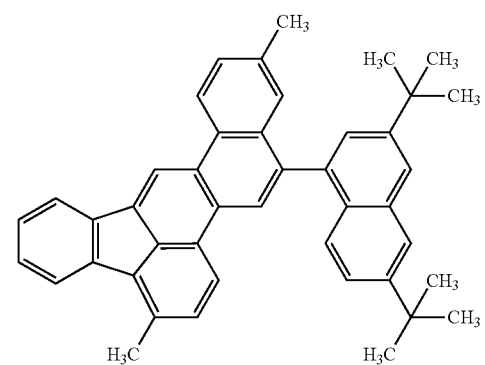
213 214
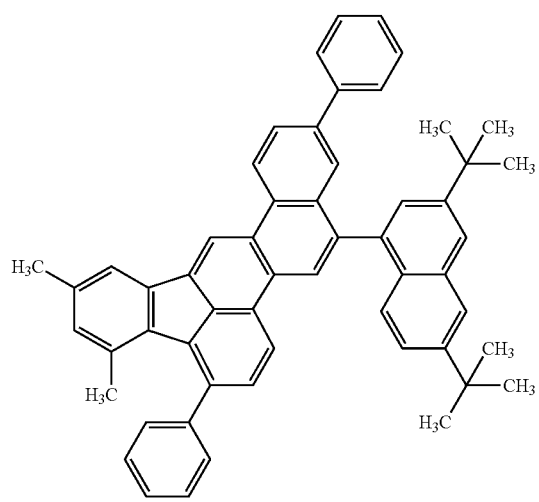
215
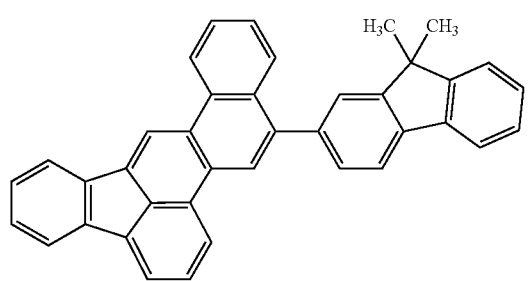
216
217
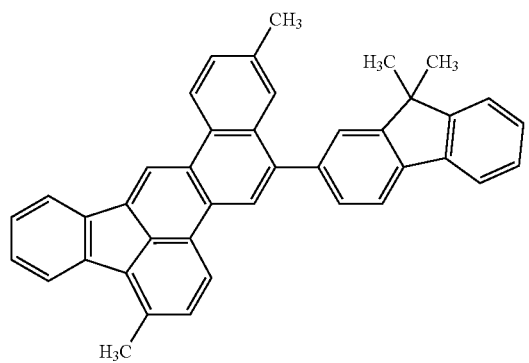
218
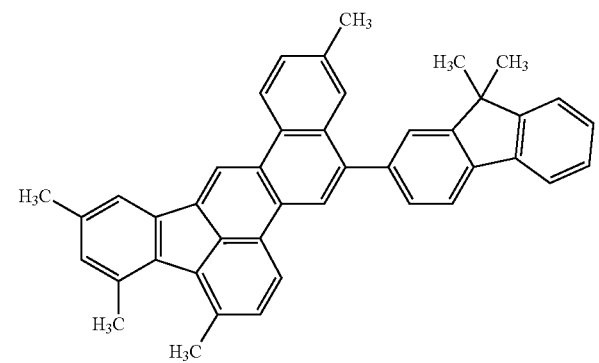

-continued
219
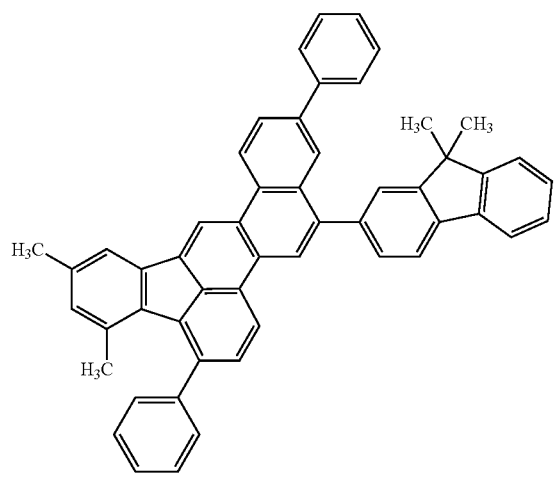
220
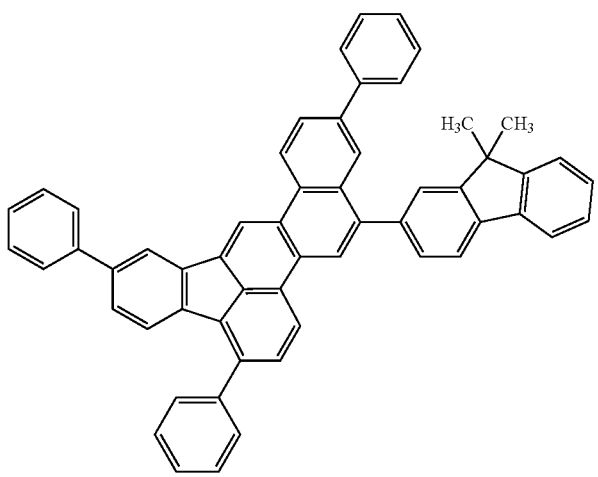
221
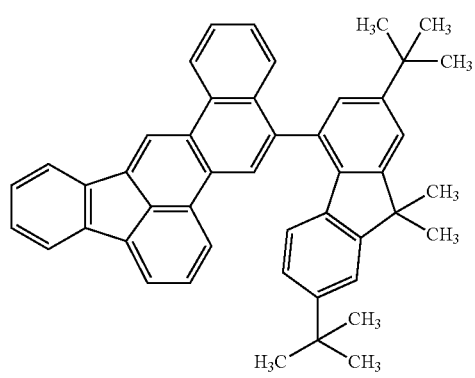
222
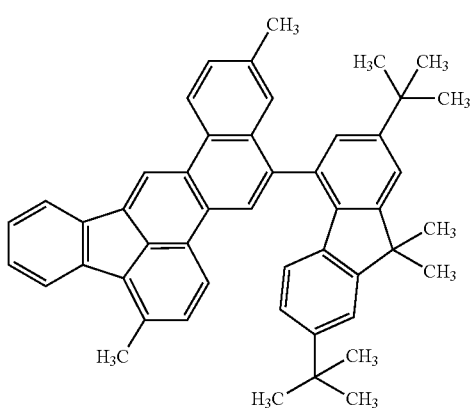
223
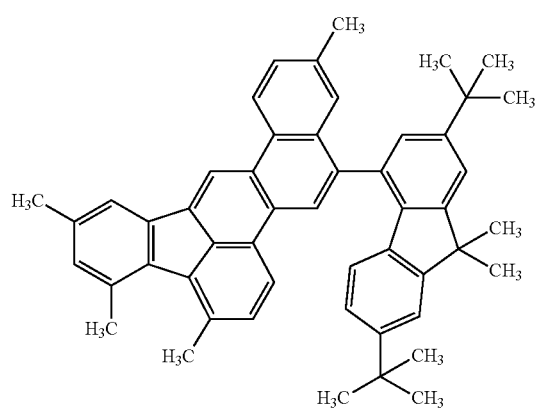
224
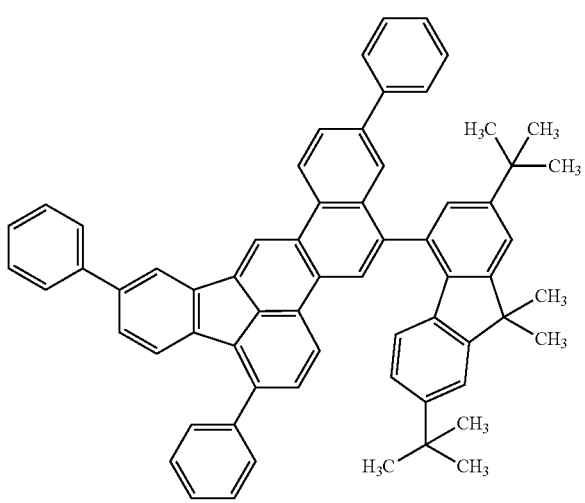

-continued
225
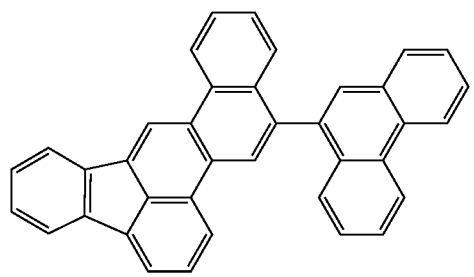
226
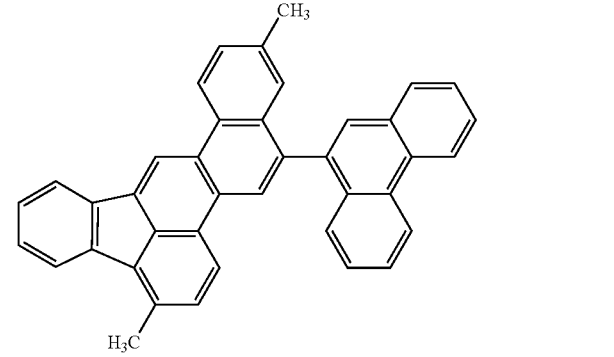
227
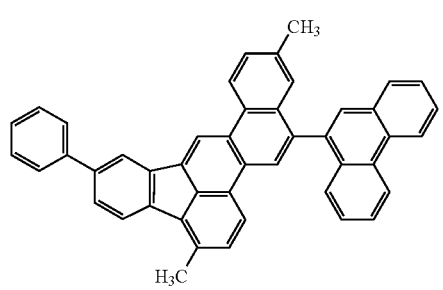
228
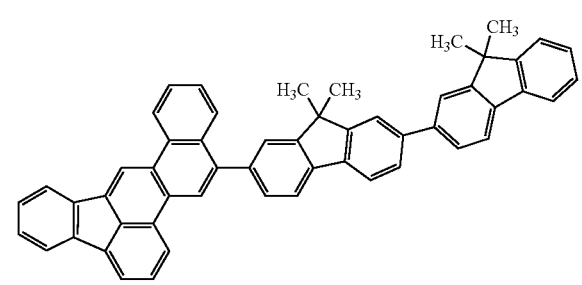
229
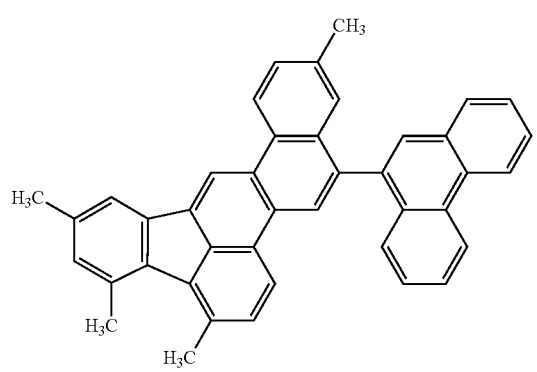
230
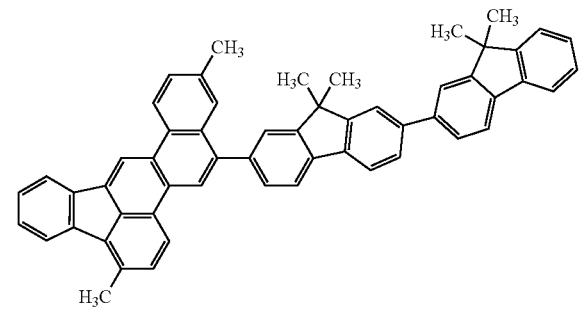
231
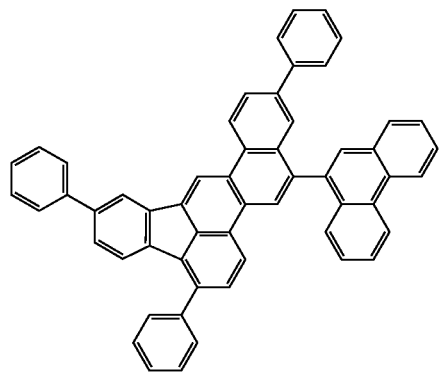
232

-continued
233
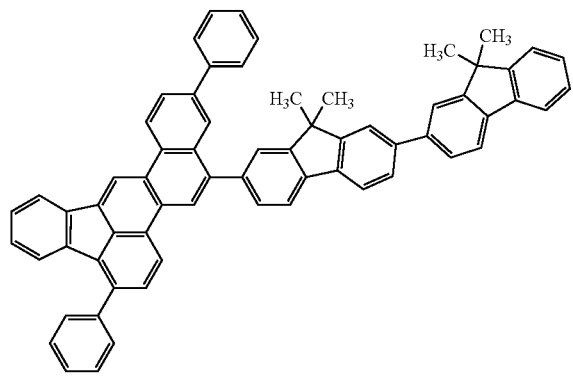
234
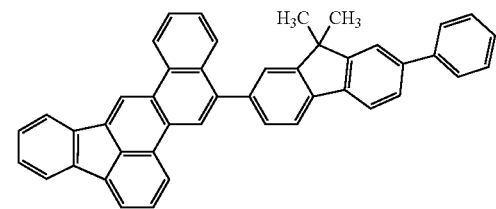
235
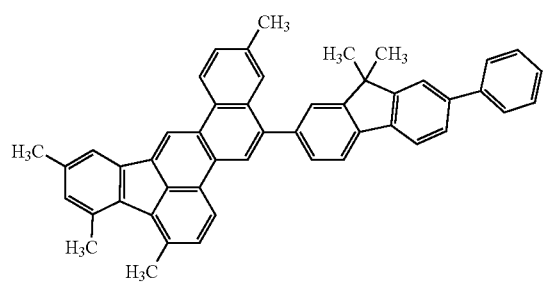
236
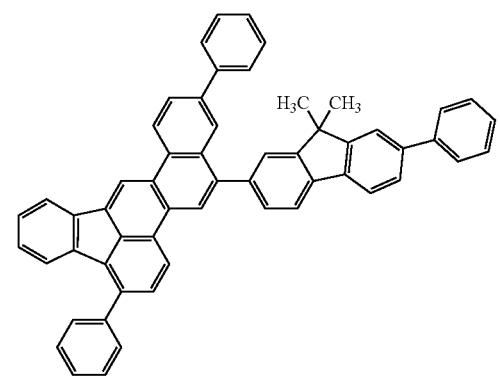
237
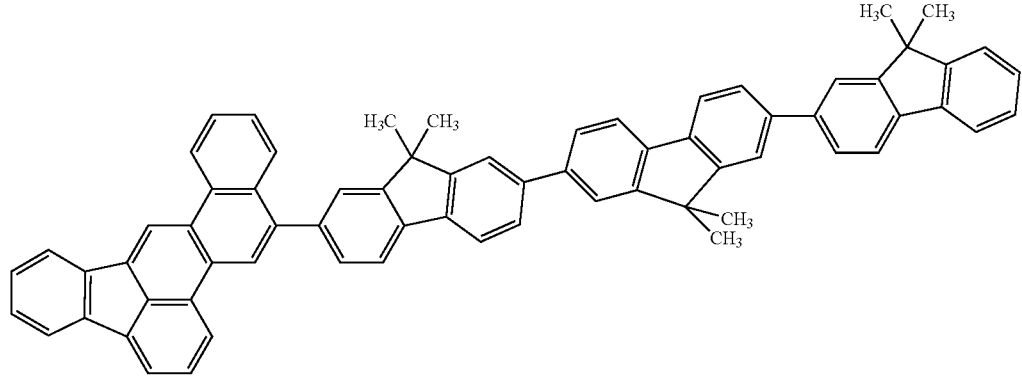
238
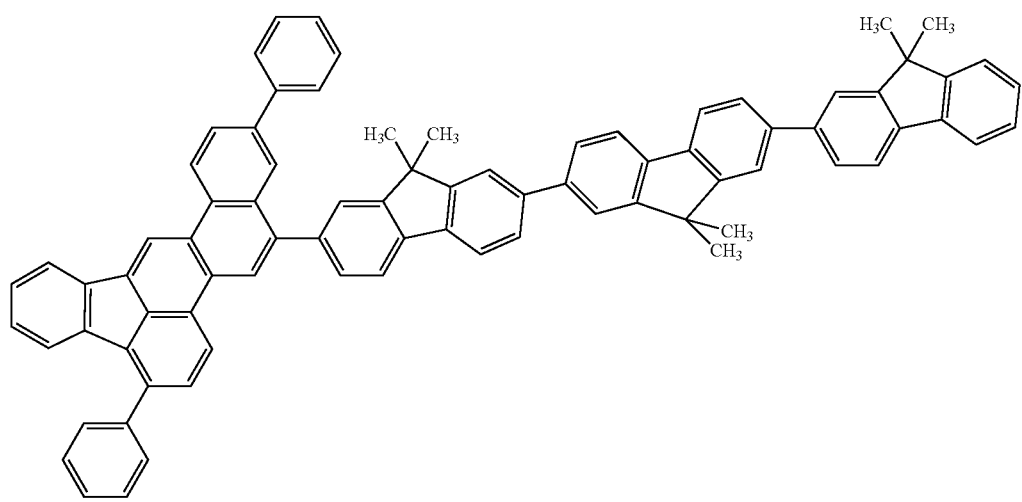

-continued
301
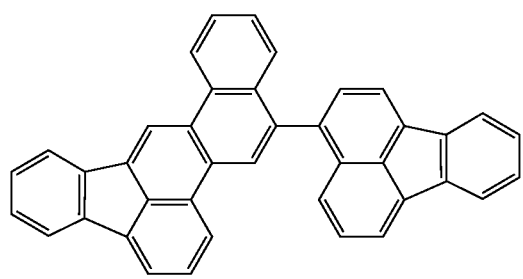
302
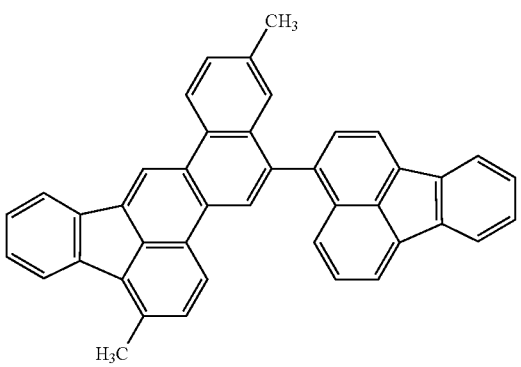
303
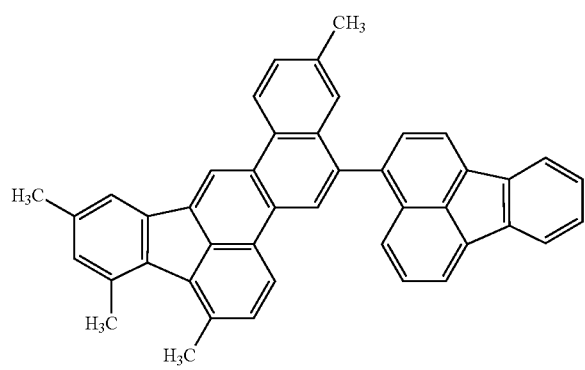
304
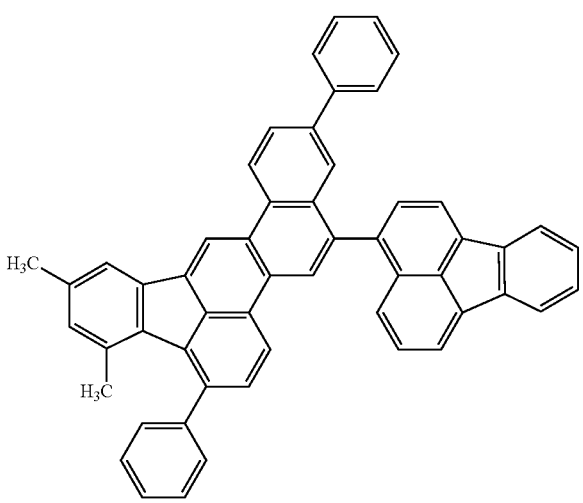
305
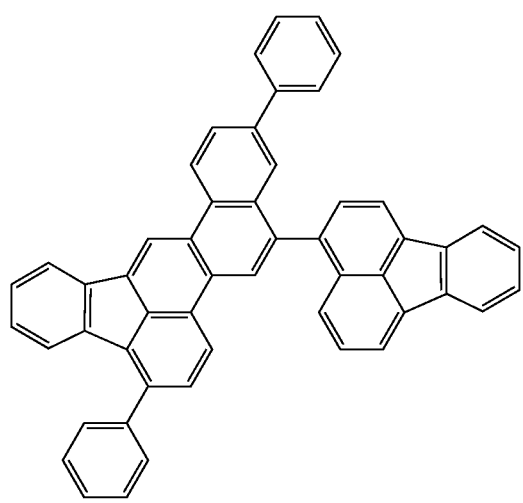
306
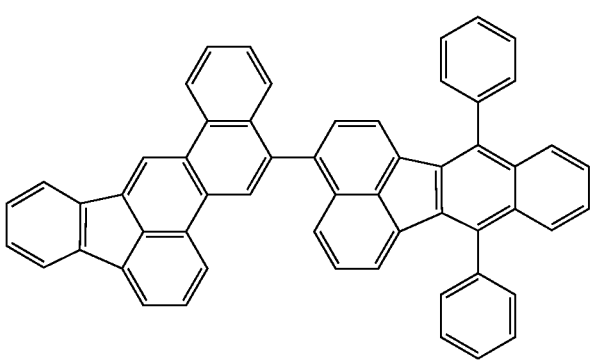

-continued
307
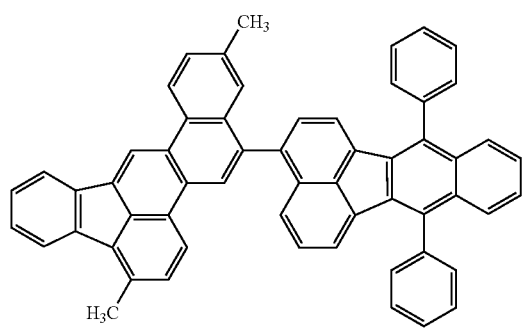
308
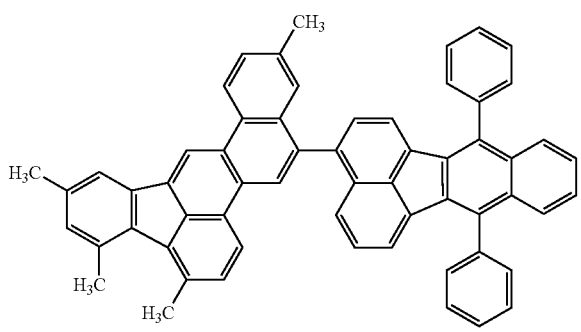
309
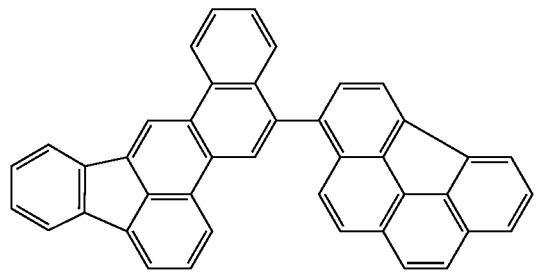
310
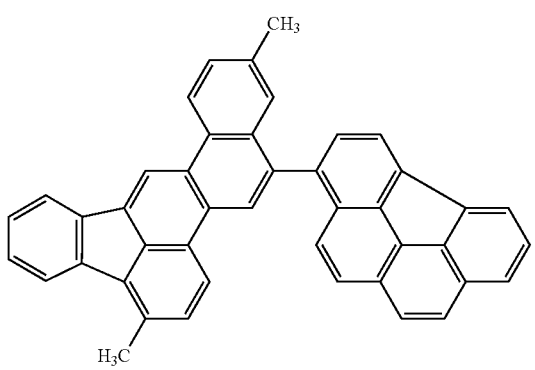
311
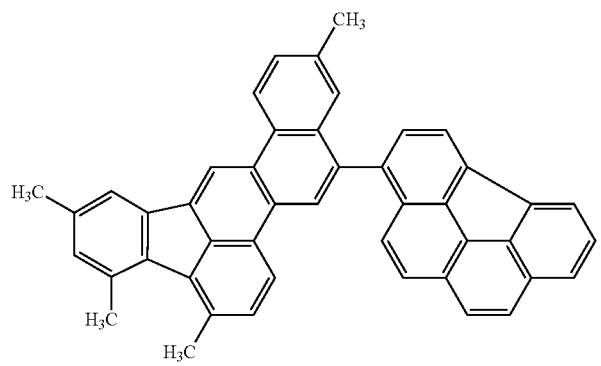
312
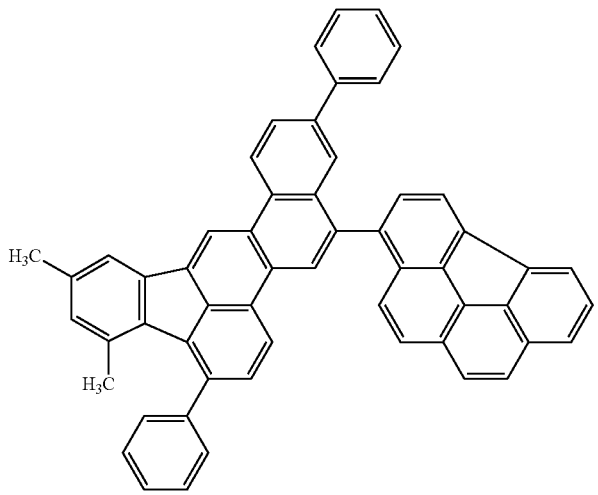
313
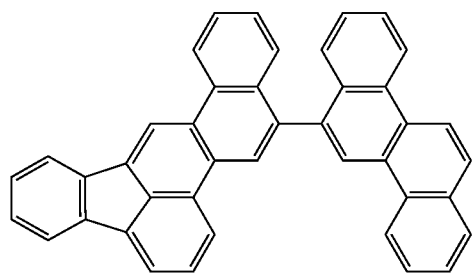
314
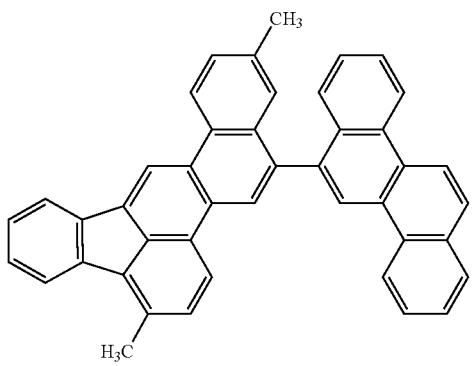

-continued
315
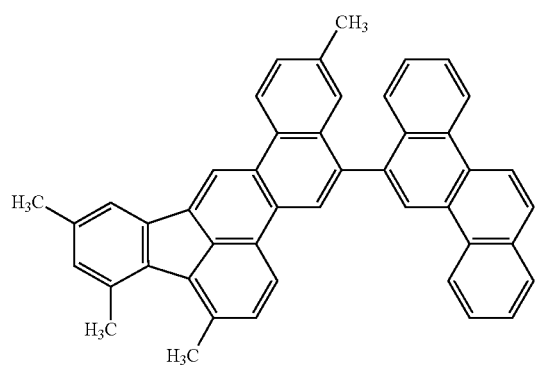
316
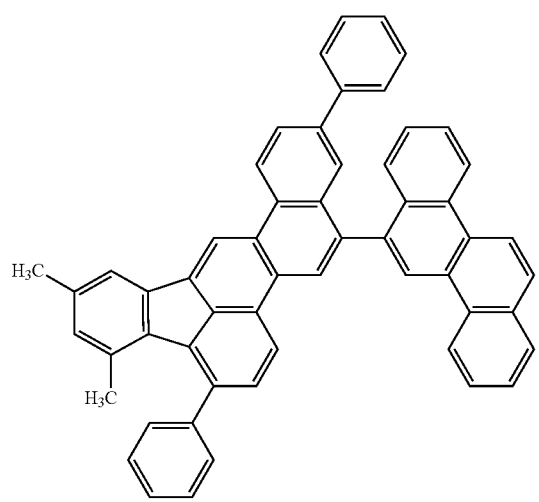
317
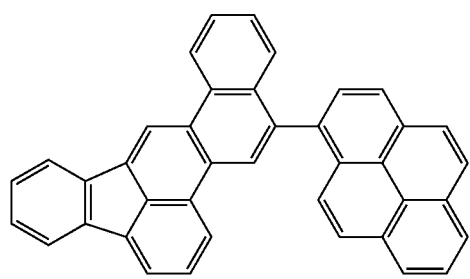
318
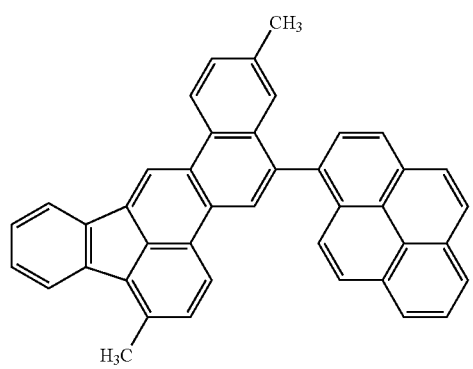
319
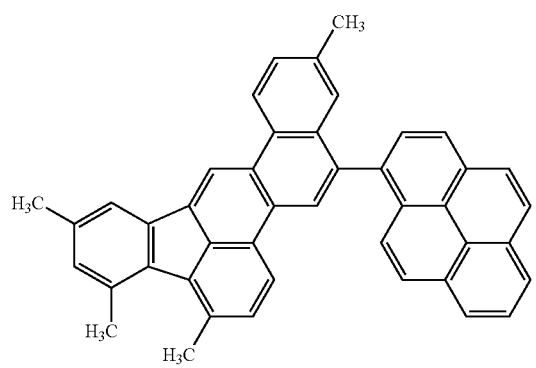
320
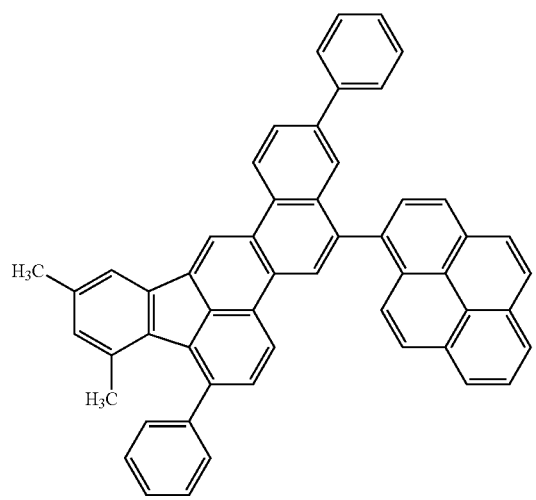

-continued
| 321 | 322 |
|---|---|
| 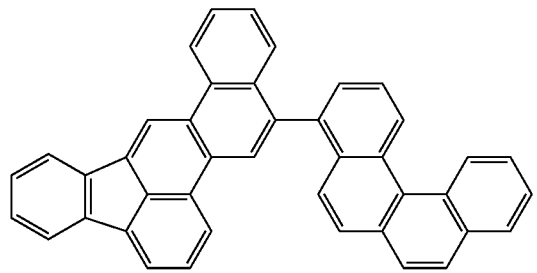 | 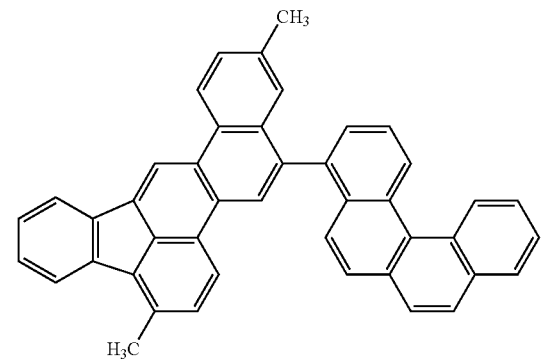 |
| 323 | 324 |
| 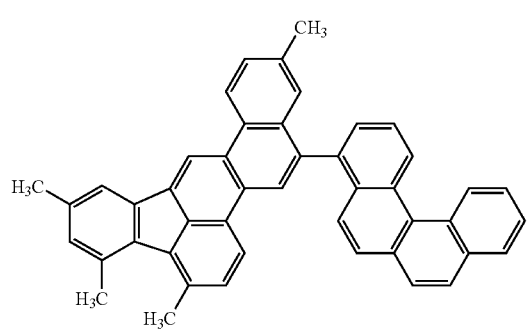 | 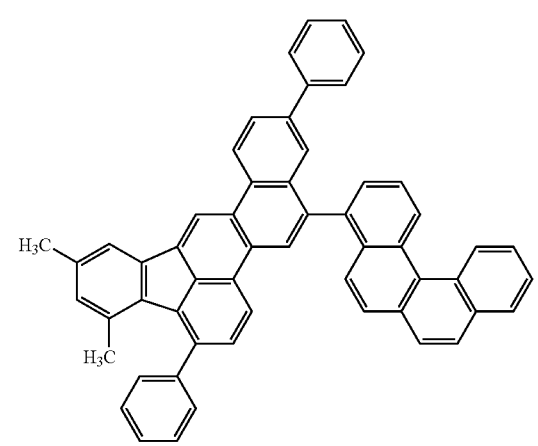 |
| 325 | 326 |
| 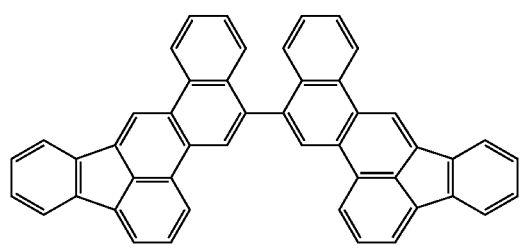 | 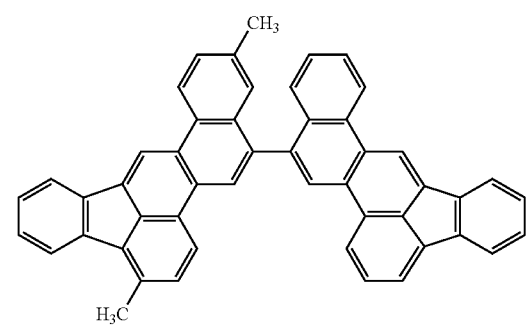 |
| 327 | 328 |
| 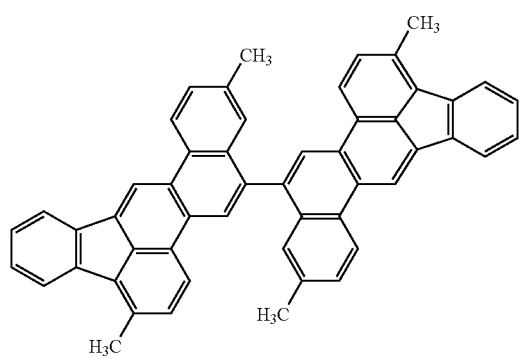 | 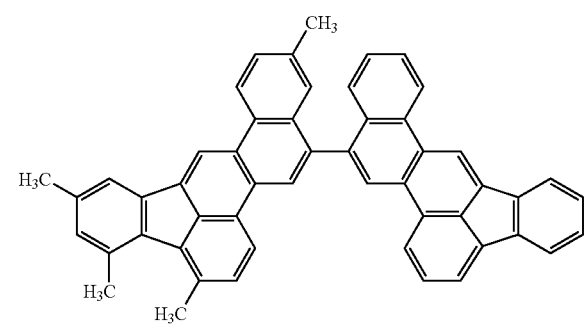 |

-continued
329
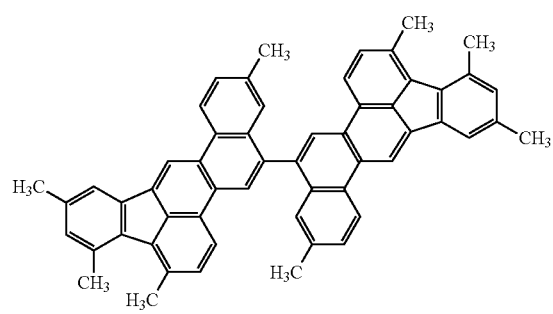
330
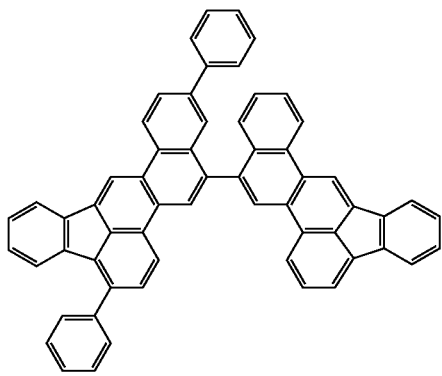
331
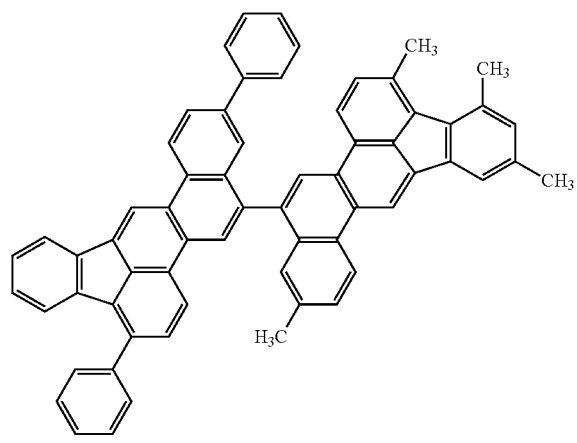
332
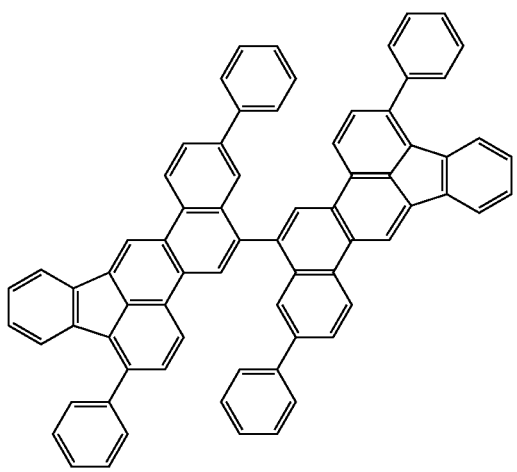
401
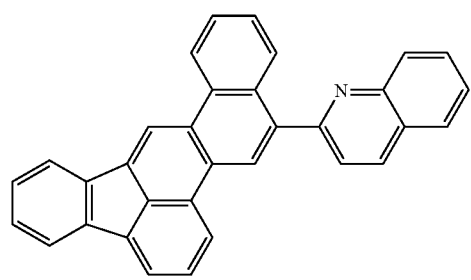
402
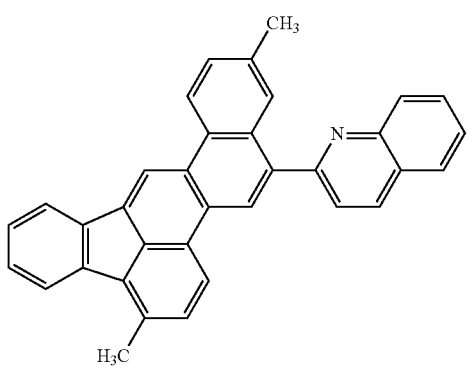

-continued
403
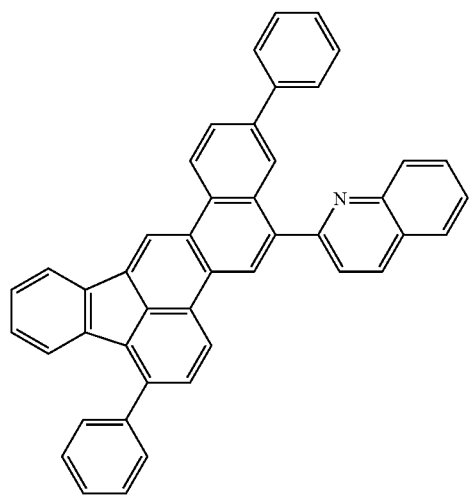
404
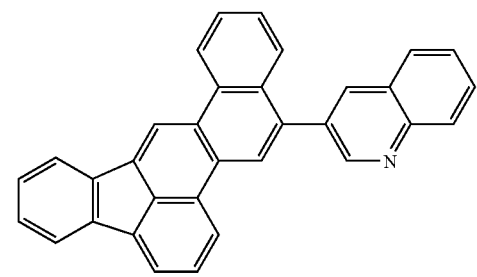
405
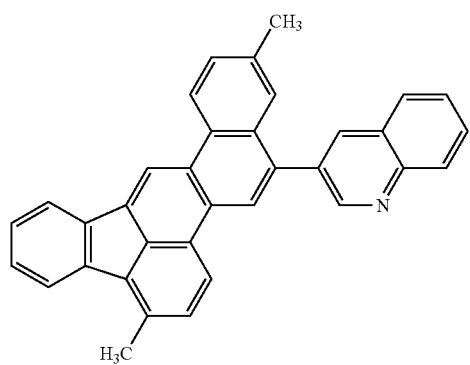
406
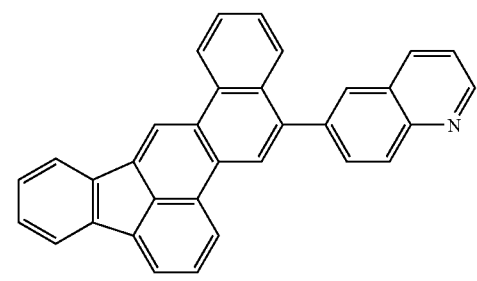
407
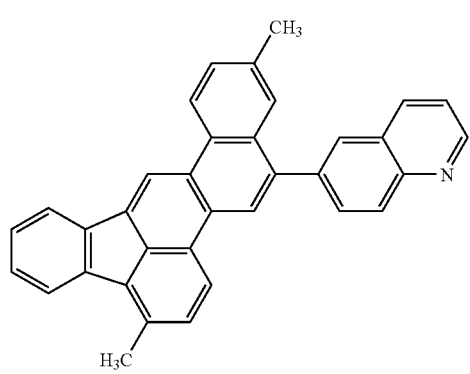
408
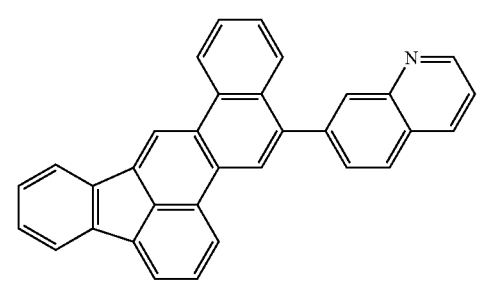
409
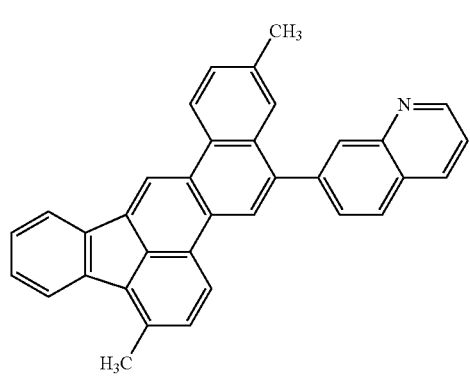
410
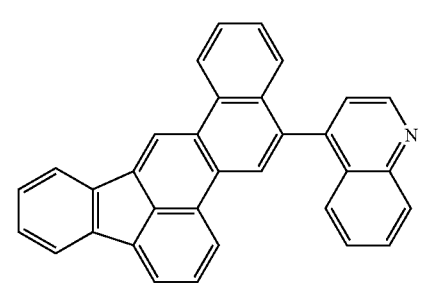

-continued
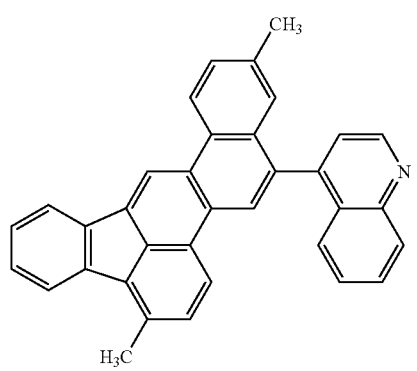
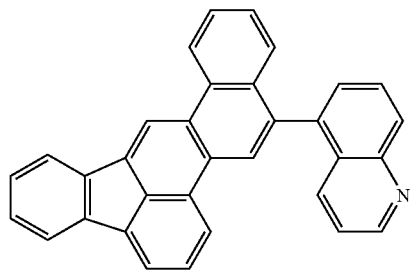
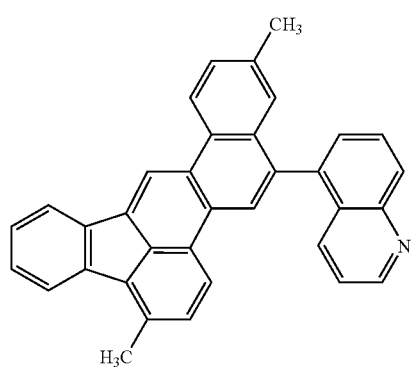
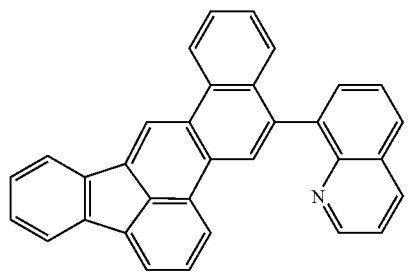
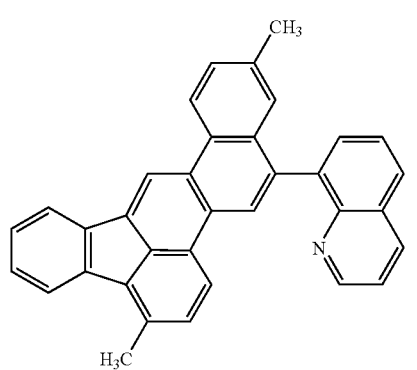
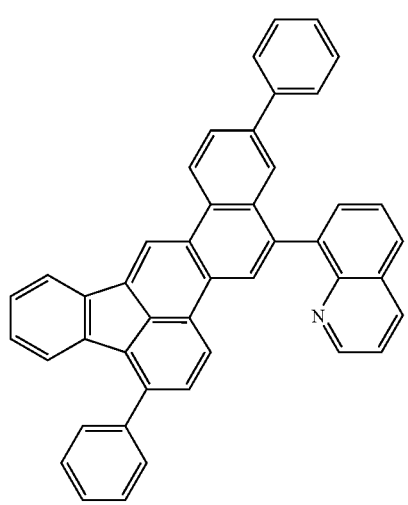
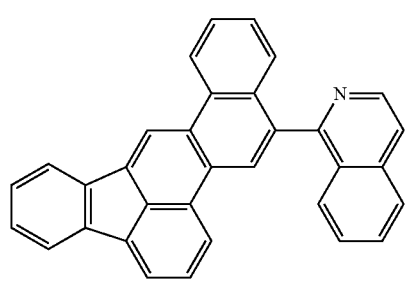
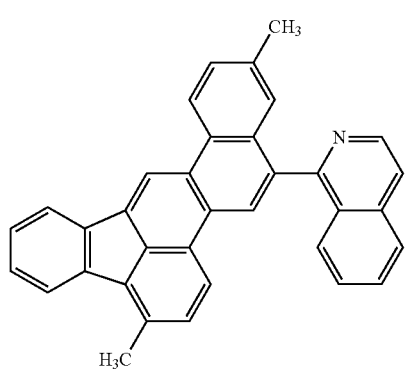

-continued
419
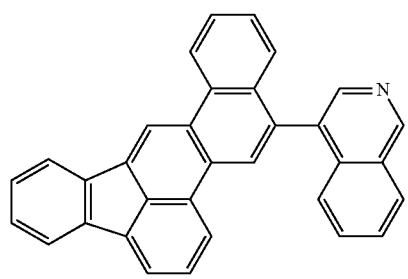
420
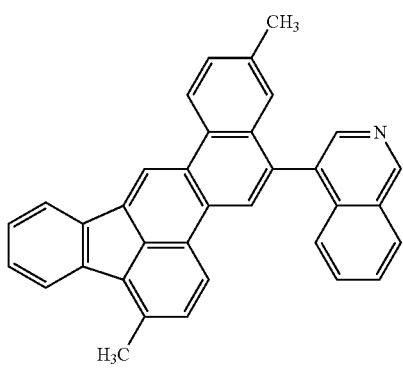
421
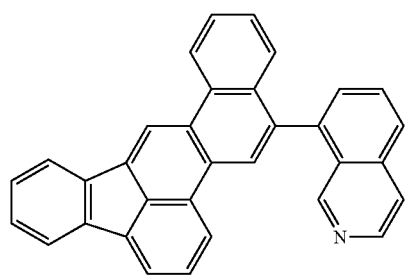
422
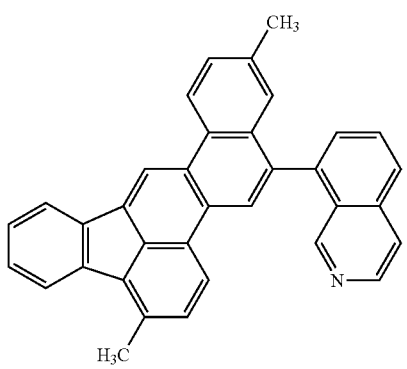
423
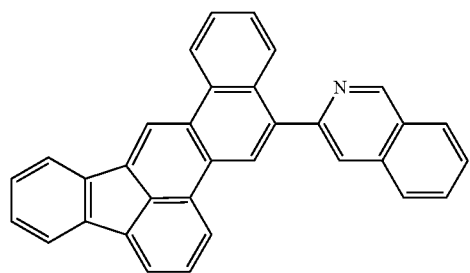
424
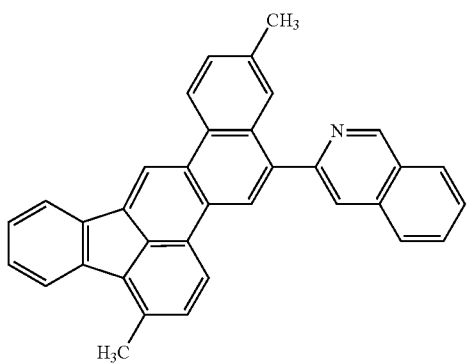
425
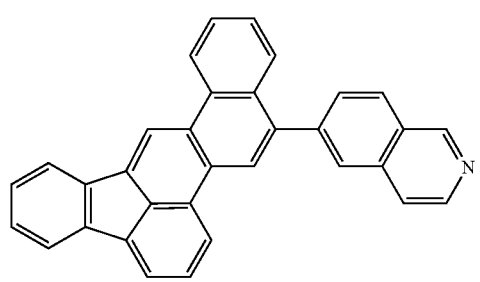
426
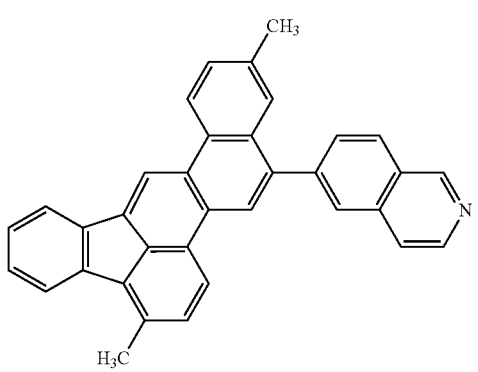

-continued
427
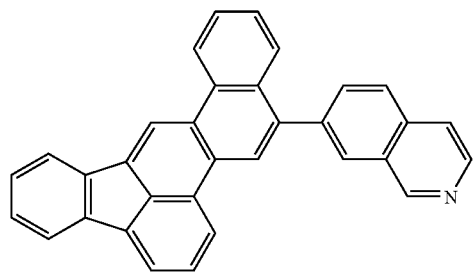
428
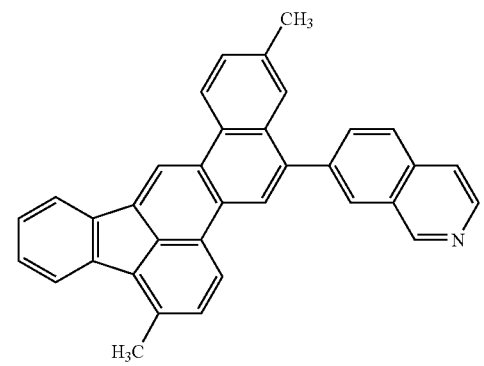
429
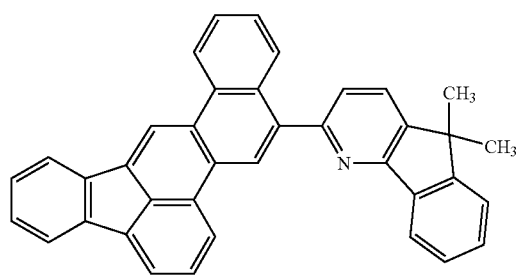
430
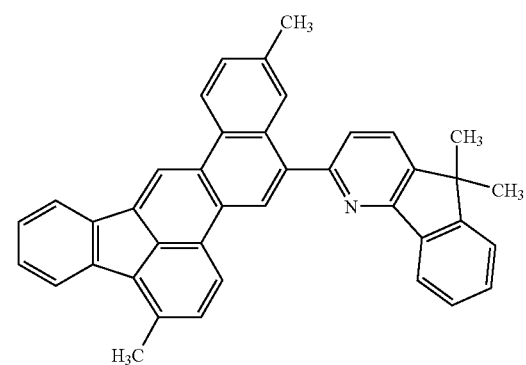
431
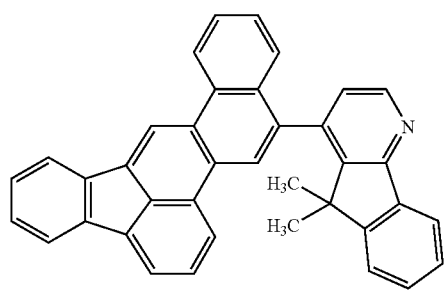
432
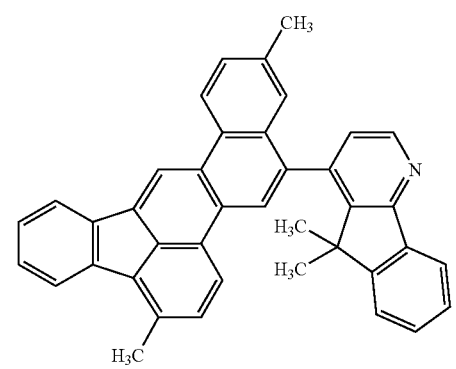
433
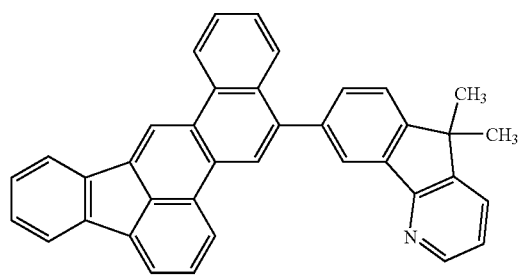
434
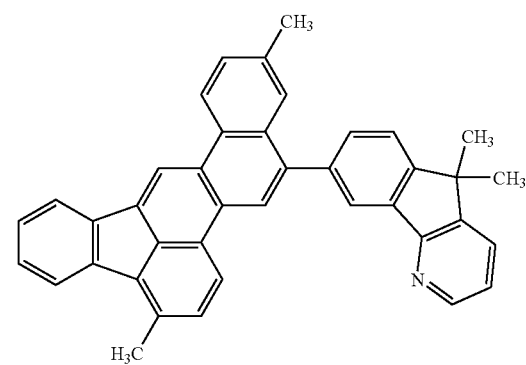

-continued
435
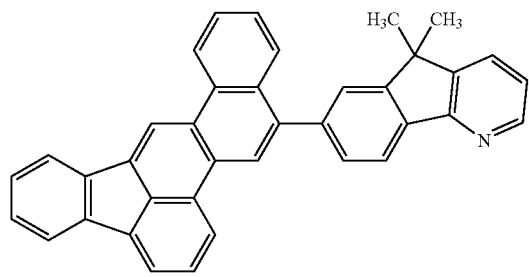
436
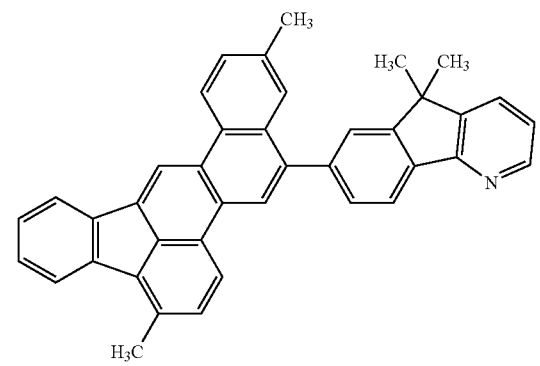
501
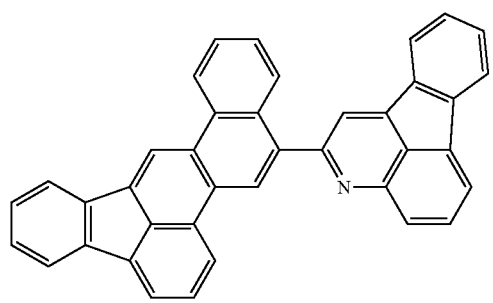
502
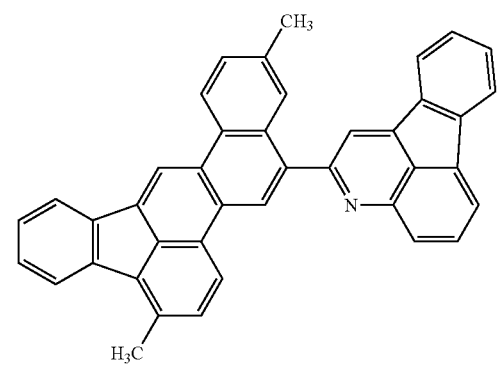
503
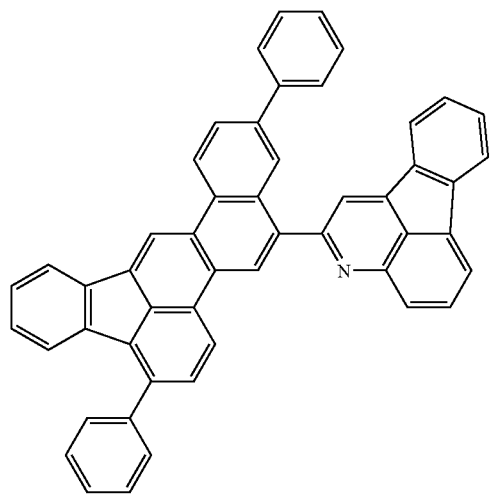
504
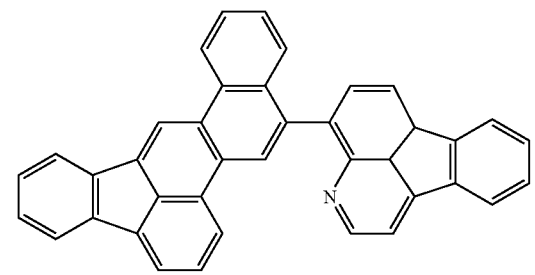
505
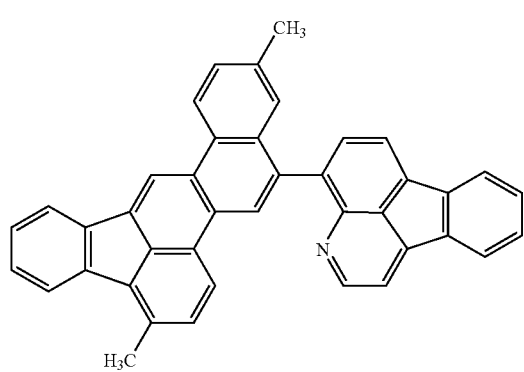
506
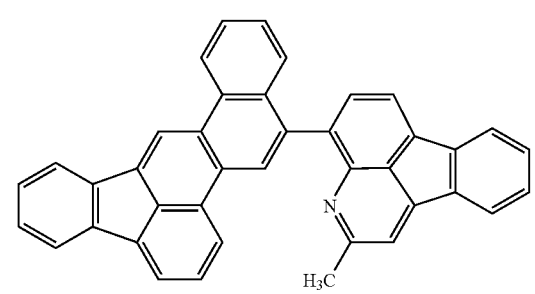

-continued
507
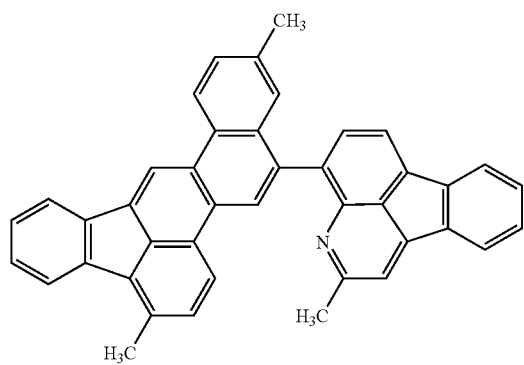
508
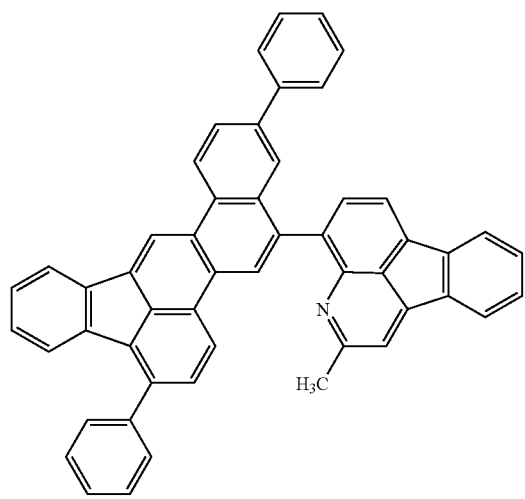
509
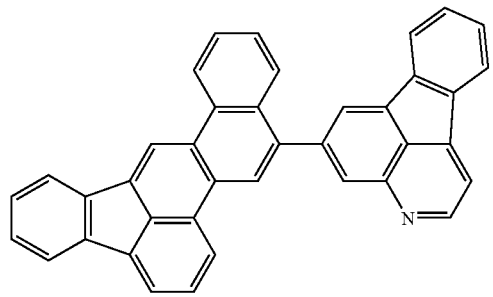
510
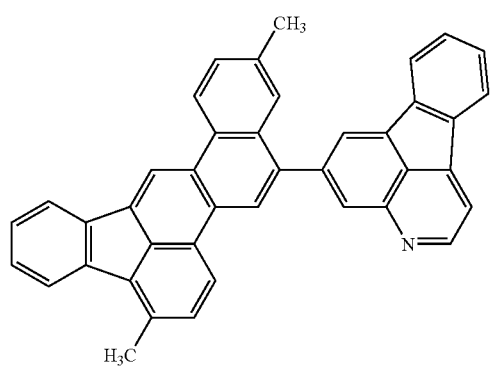
511
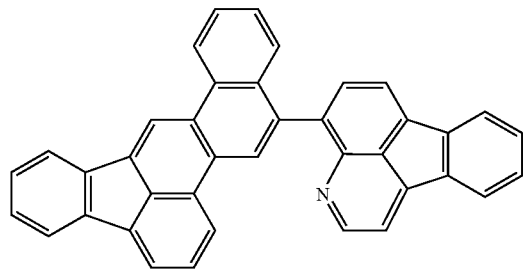
512
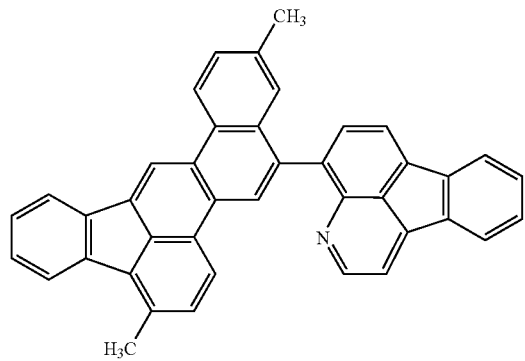
513
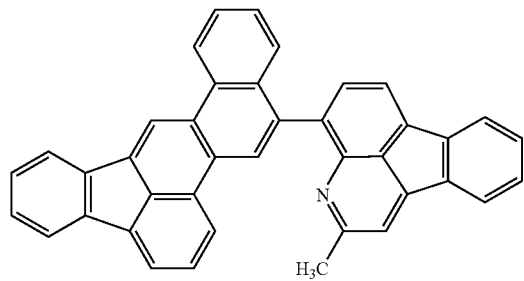
514
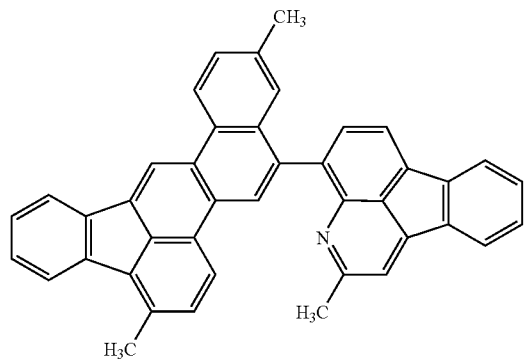

-continued
515 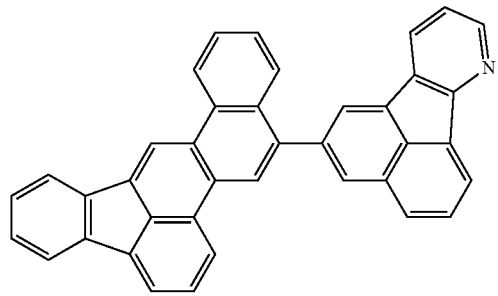
516 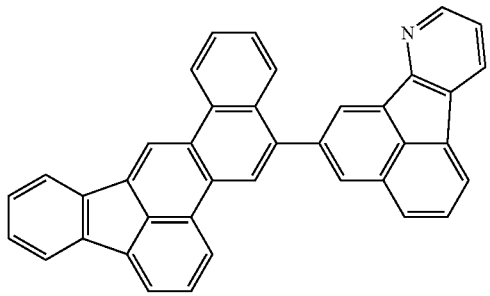
517 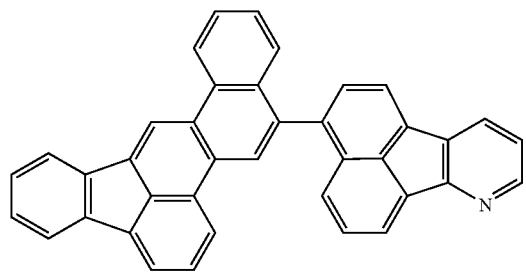
518 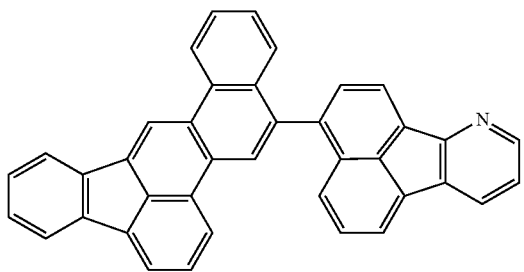
519 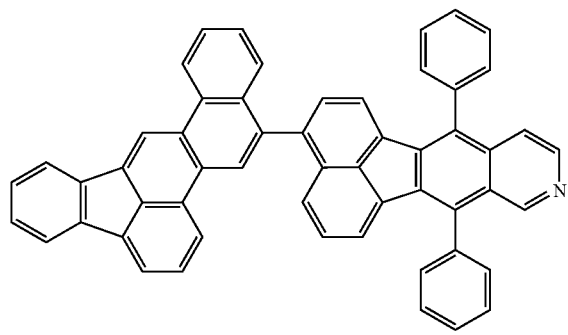
520 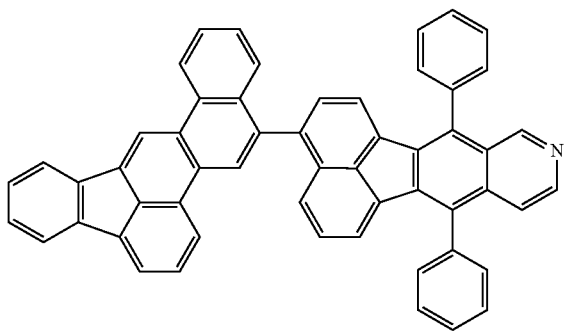
521 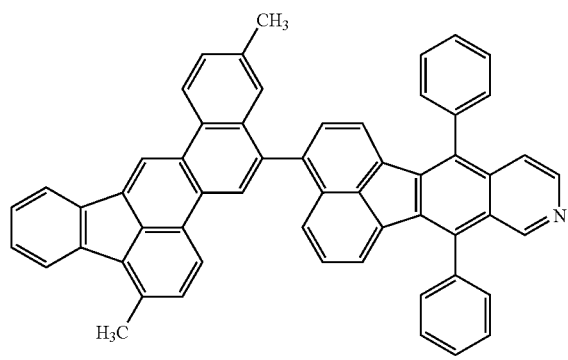
522 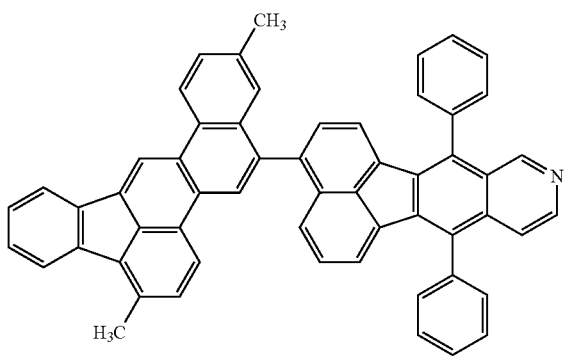
523 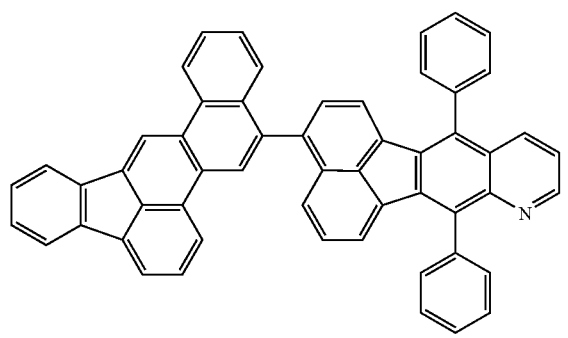
524 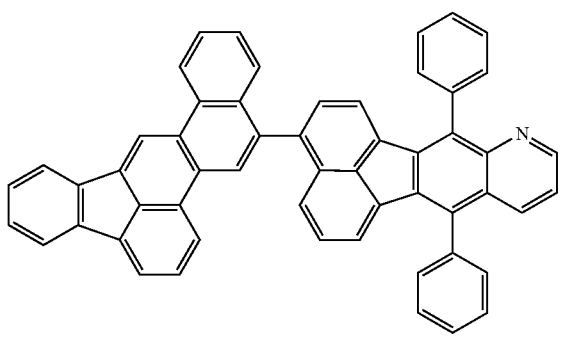

-continued
525
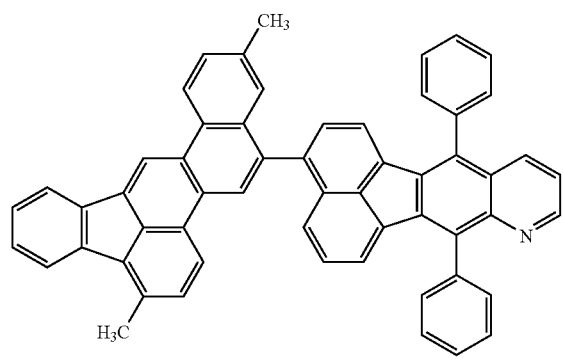
526
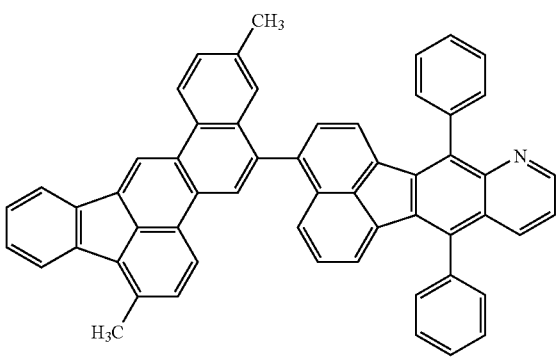
601
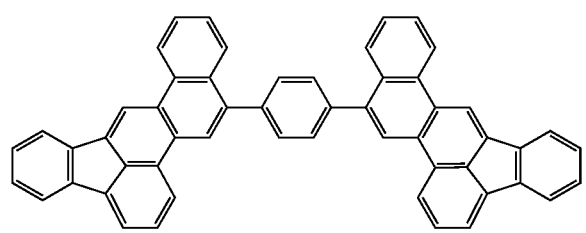
602
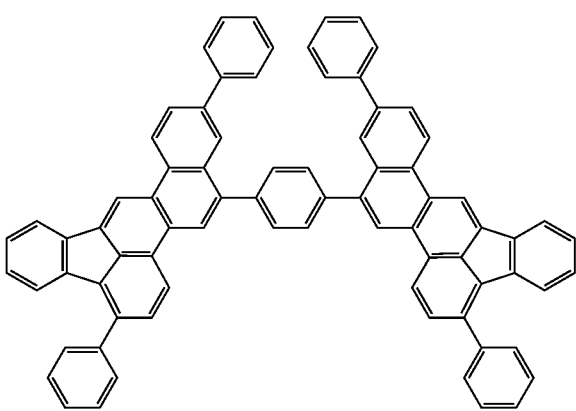
603
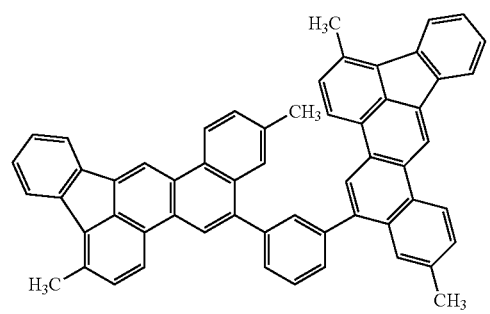
604
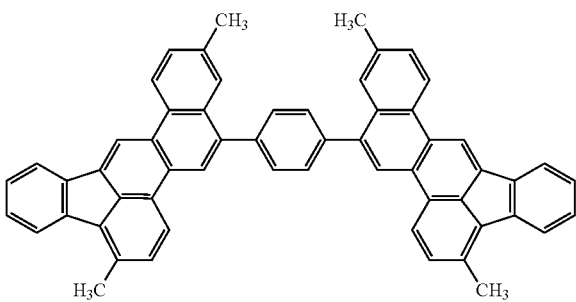
605
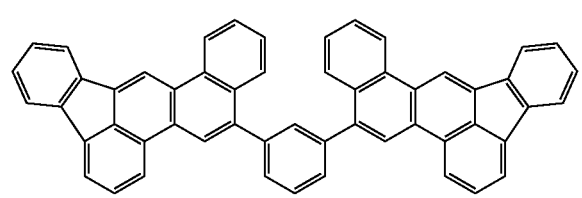
606
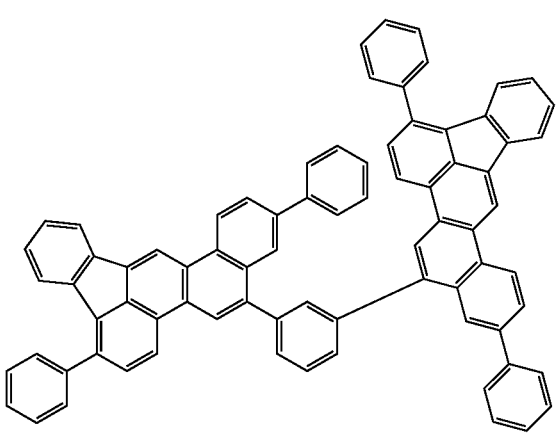

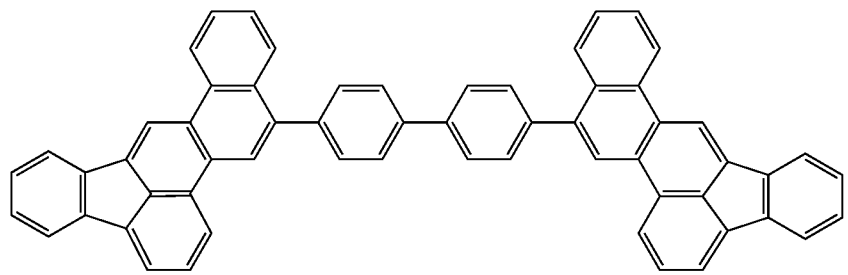
607
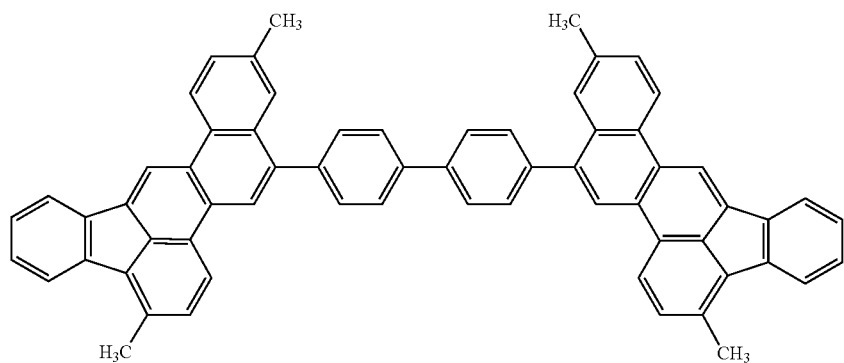
608
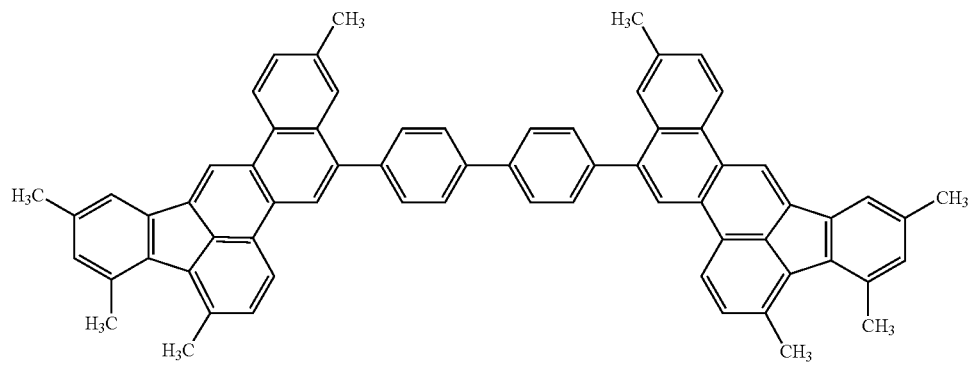
609
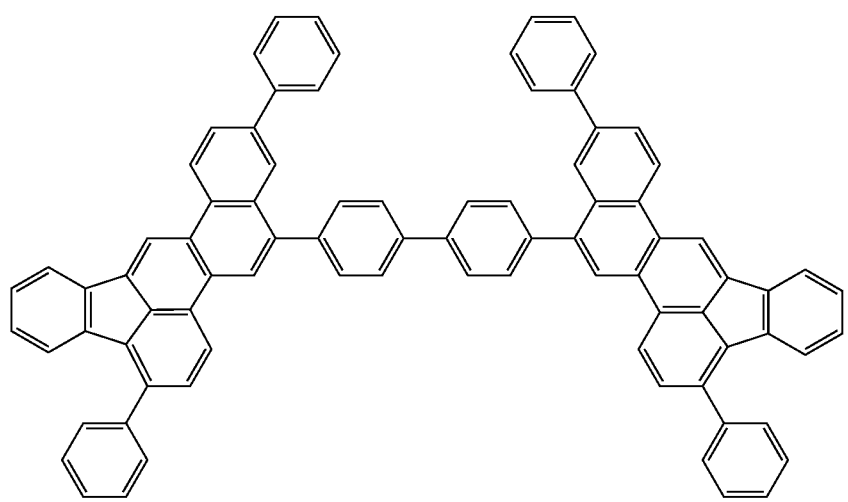
610

-continued
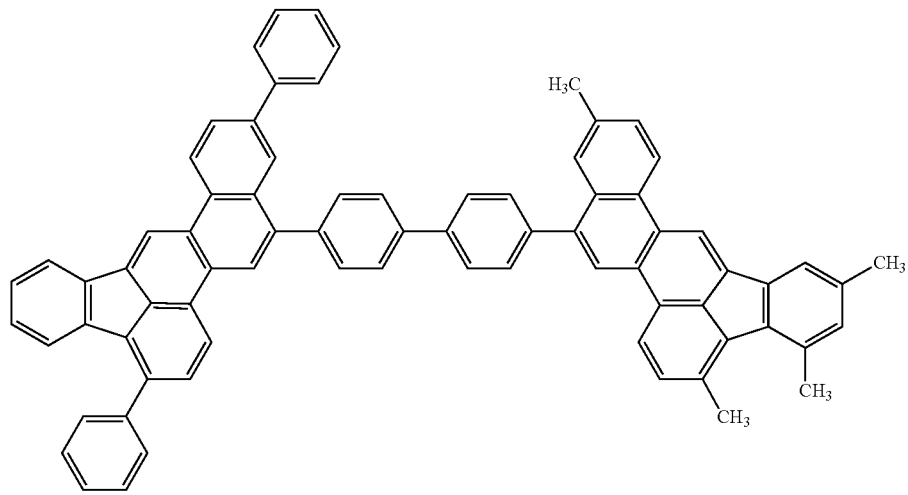
611
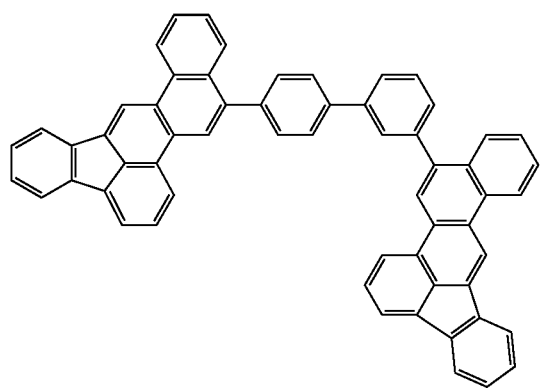
612
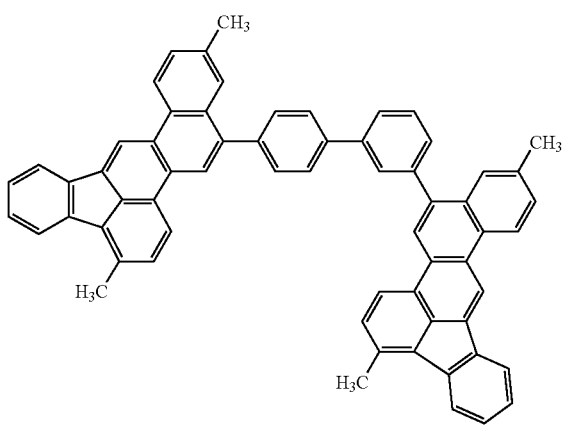
613
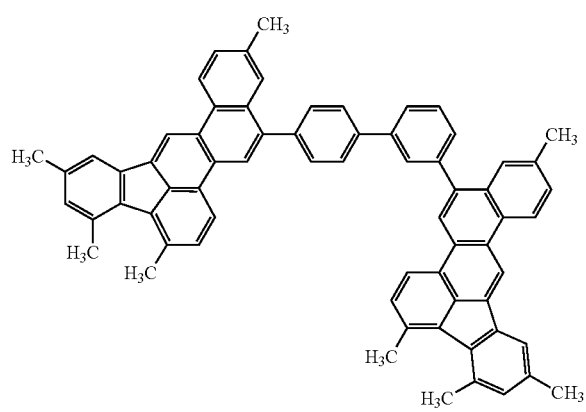
614
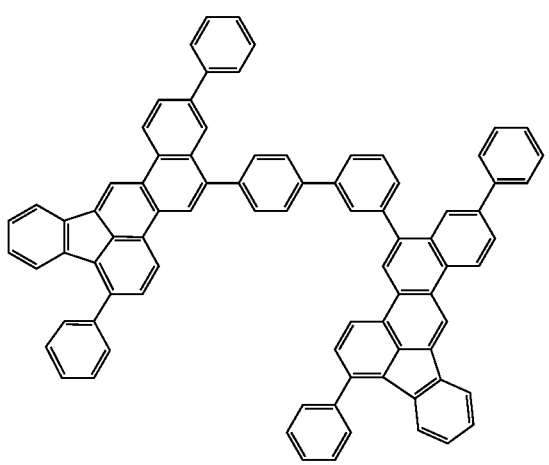
615

-continued
616
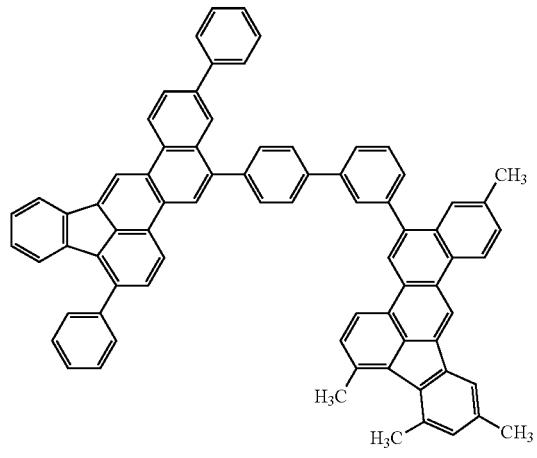
617
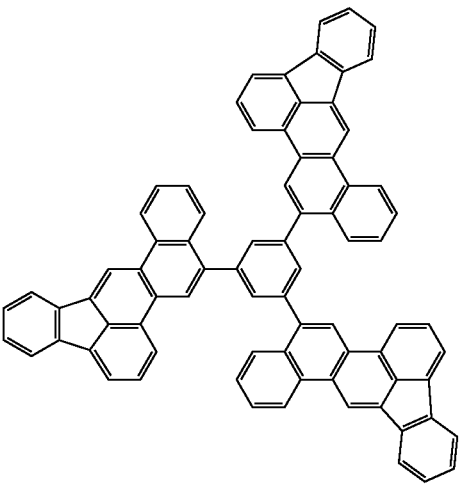
701
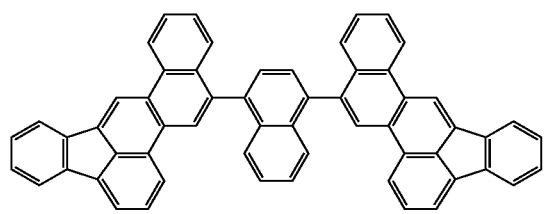
702
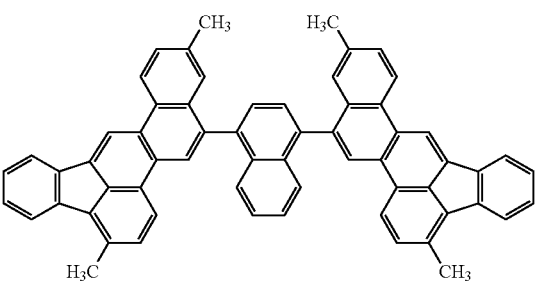
703
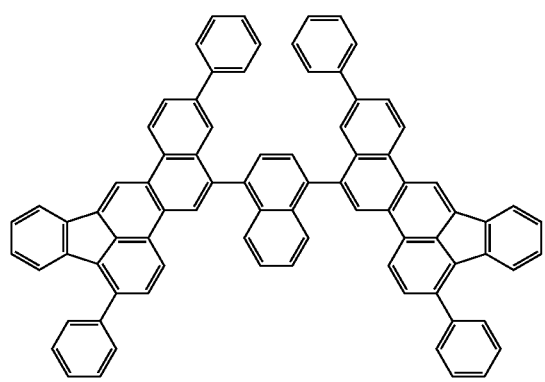
704
705
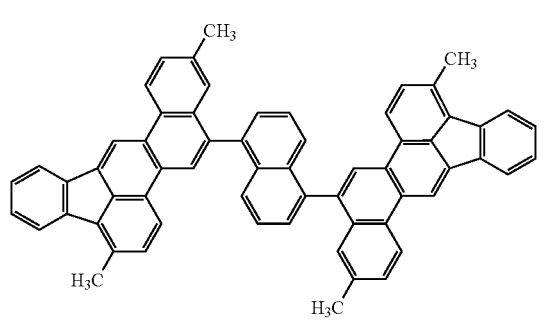
706
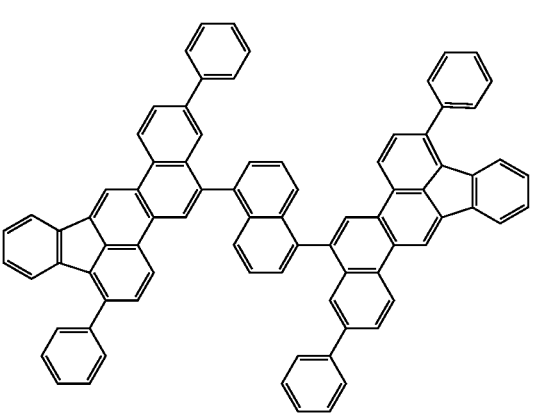

-continued
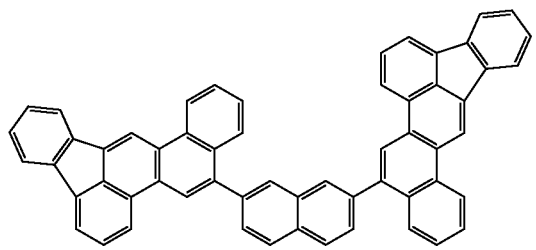
707
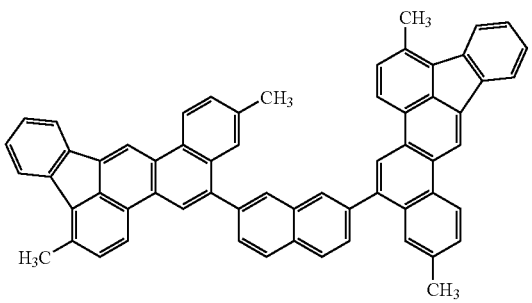
708
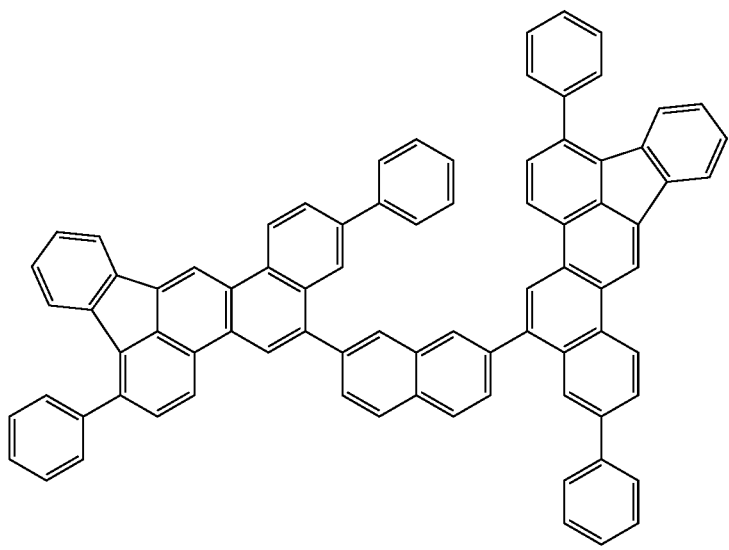
709
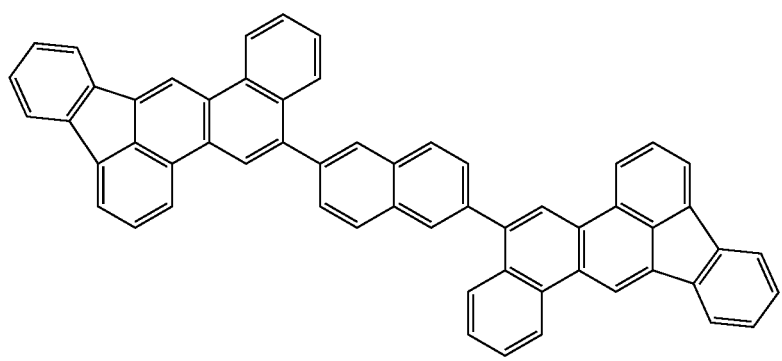
710
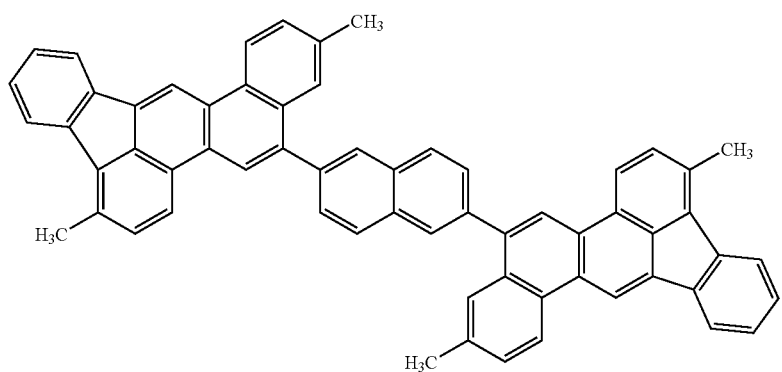
711

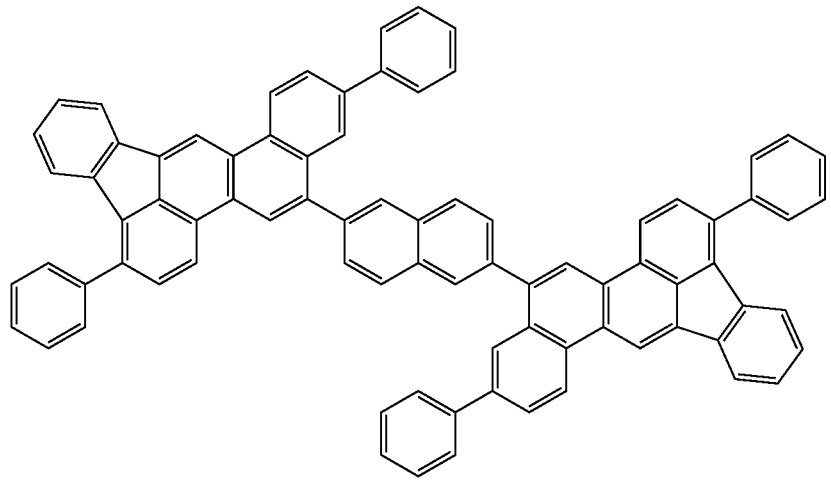
712
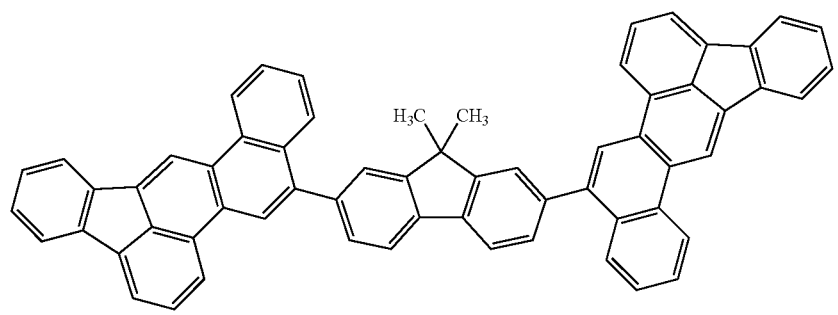
713
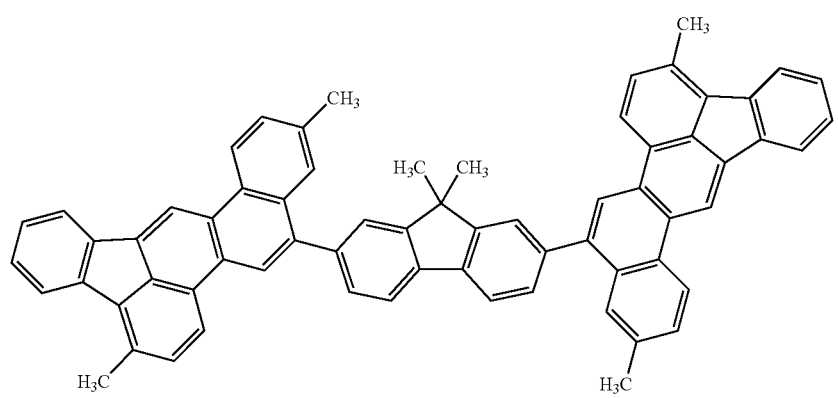
714
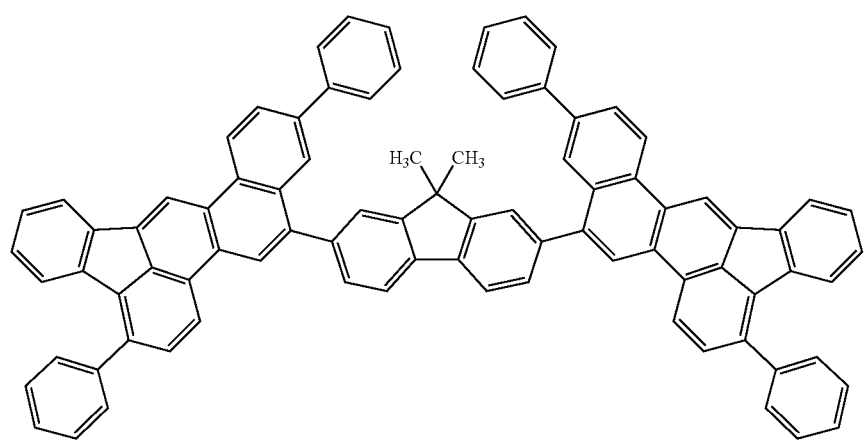
715

716
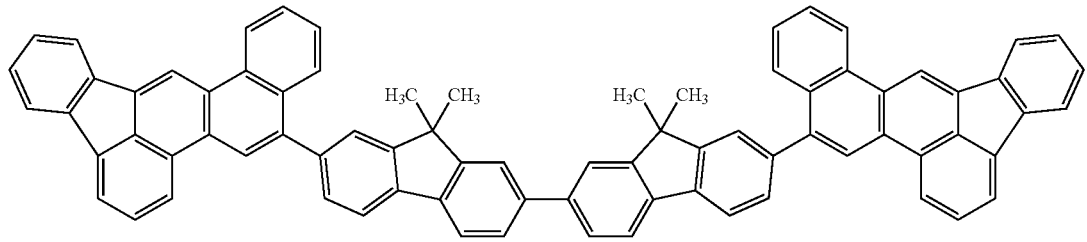
717
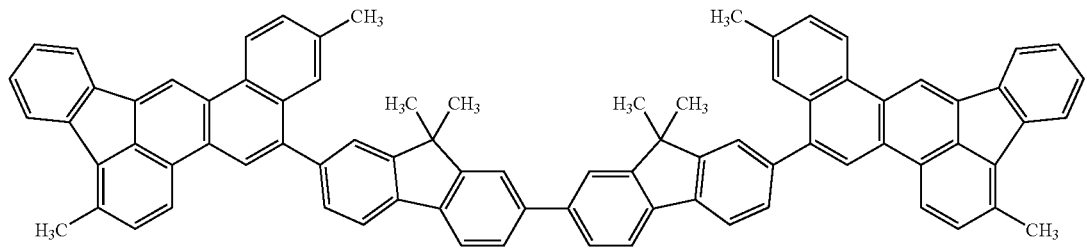
718
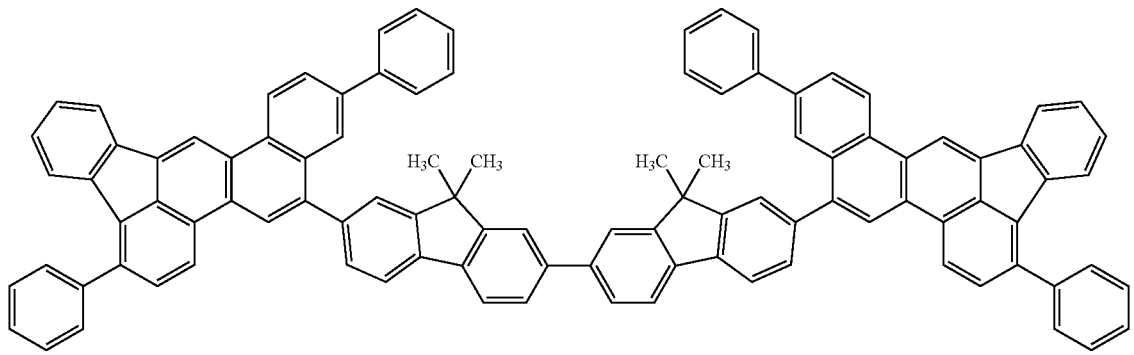
719 720
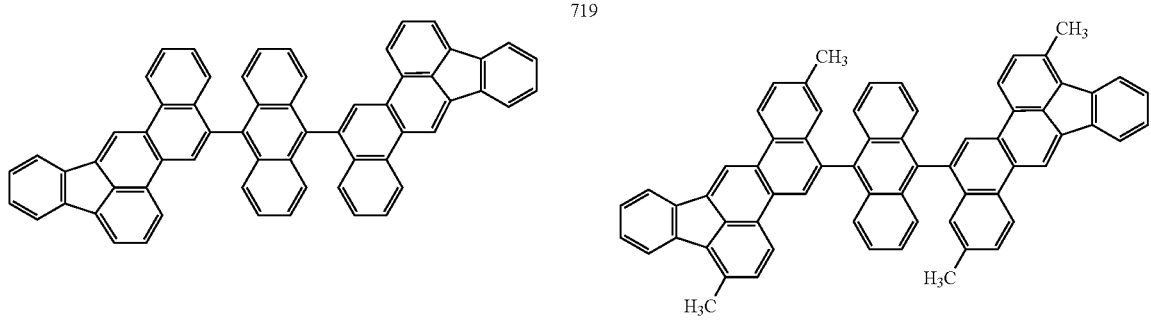
721 722
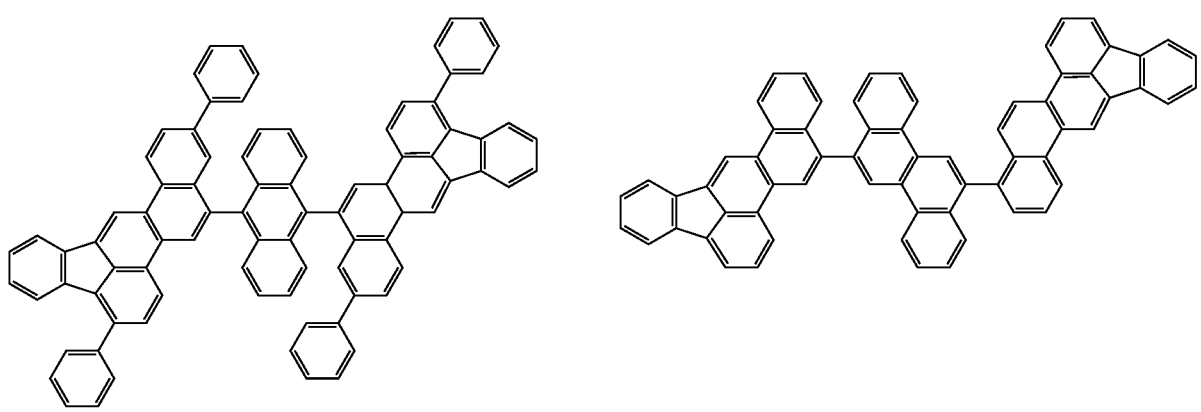

-continued

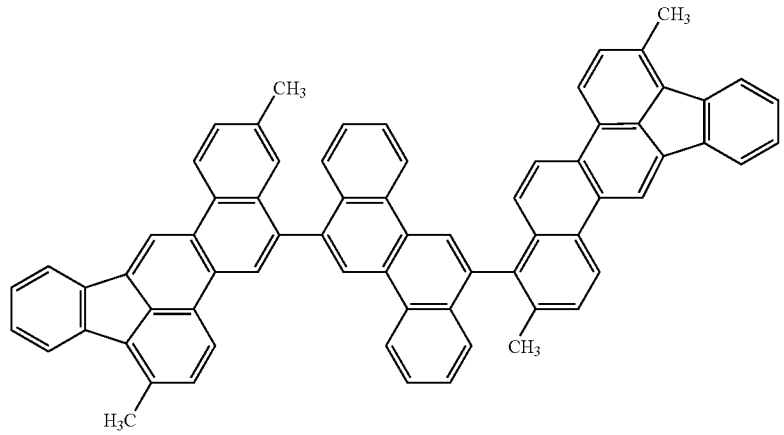
723

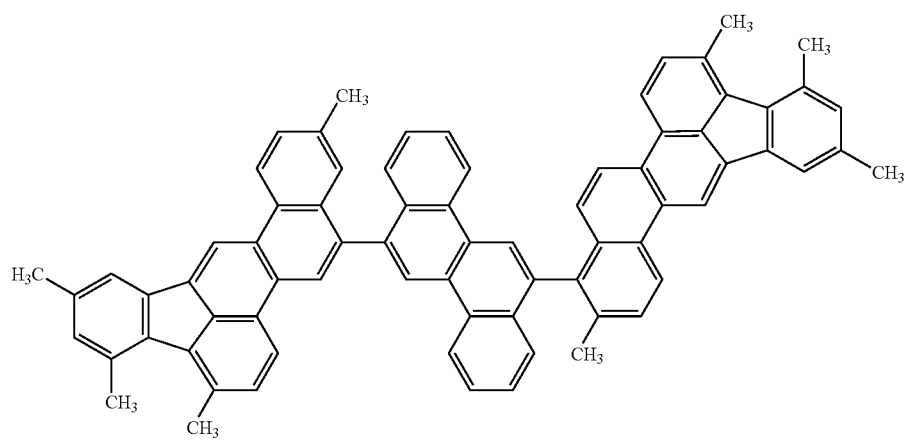
724

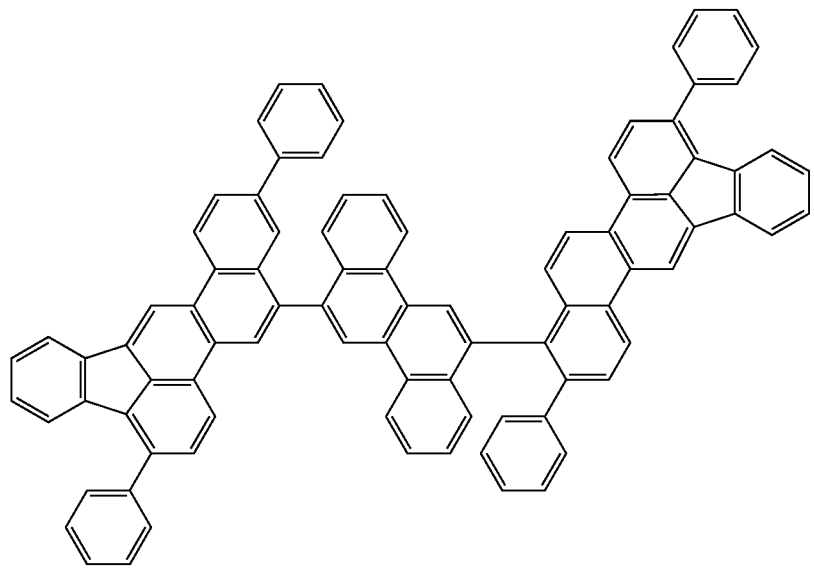
725

Next, the organic light-emitting device of the present invention will be described in detail.

The organic light-emitting device of the present invention is constituted of an anode, a cathode, and a layer formed of an organic compound and interposed between the anode and the cathode. Further, either one of the anode and the cathode is formed of a transparent or translucent electrode material.

The organic light-emitting device of the present invention may have, between the cathode and the anode, another layer formed of another organic compound in addition to the above layer formed of the organic compound. The term "layer formed of an organic compound" herein employed refers to, for example, a hole-transporting layer, an electron-transporting layer, a hole injection layer, or a hole/exciton blocking layer for blocking holes and/or excitons.

The organic light-emitting device according to the present invention may appropriately have those other layers each formed of another organic compound.

In addition, the organic light-emitting device of the present invention is preferably an electroluminescent device that emits light by applying a voltage between an anode and a cathode.

Hereinafter, the organic light-emitting device of the present invention will be described in detail with reference to the drawings.

First, reference numerals used in the figures will be described. Reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole injection layer, reference numeral 8 denotes a hole/exciton blocking layer, and reference numerals 10, 20, 30, 40, 50, and 60 each denote an organic light-emitting device.

FIG. 1 is a schematic cross-sectional view illustrating a first embodiment of the organic light-emitting device of the present invention. In the organic light-emitting device 10 shown in FIG. 1, there are sequentially provided on a substrate 1, an anode 2, a light-emitting layer 3 and a cathode 4. The configuration of the organic light-emitting device 10 is useful when the light-emitting layer 3 is composed of a compound having all of hole transporting ability, electron transporting ability and light emitting ability. Further, the configuration is also useful when the light-emitting layer 3 is composed of a mixture of compounds having the characteristics of any one of hole transporting ability, electron transporting ability, and light emitting ability.

Figure 2:
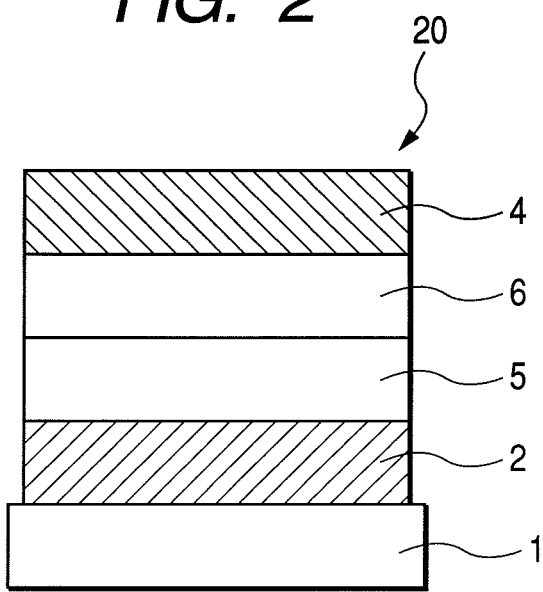
FIG. 2 is a cross sectional view illustrating an organic light-emitting device according to a second embodiment of the present invention.

FIG. 2 is a schematic cross-sectional view illustrating a second embodiment of the organic light-emitting device of the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 is useful when a light-emitting compound having either one of hole transporting ability and electron transporting ability and an organic compound having only electron transporting ability or hole transporting ability are used in combination. Incidentally, in the organic light-emitting device 20 shown in FIG. 2, the hole-transporting layer 5 and the electron-transporting layer 6 each serve also as a light-emitting layer.

Figure 3:
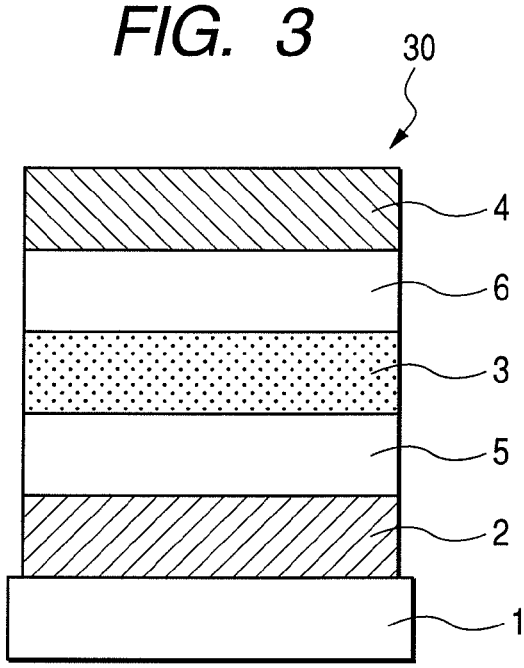
FIG. 3 is a cross sectional view illustrating an organic light-emitting device according to a third embodiment of the present invention.

FIG. 3 is a schematic cross-sectional view illustrating a third embodiment of the organic light-emitting device of the present invention. The organic light-emitting device 30 shown in FIG. 3 is different from the organic light-emitting device 20 shown in FIG. 2 in that a light-emitting layer 3 is additionally provided between a hole-transporting layer 5 and an electron-transporting layer 6. The organic light-emitting device 30 has a configuration in which the functions of carrier transportation and light emission are separated from each other, so that organic compounds having characteristics of hole-transporting property, electron-transporting property and light-emitting property, respectively, can suitably be combined and used. Therefore, since the degree of freedom in selecting materials can significantly be increased, and further since various organic compounds having different emission wavelengths can be used, a wide variety of emission hues can be provided. Further, it also becomes possible to effectively confine carriers or excitons in the light-emitting layer 3 at the central portion, thereby improving the emission efficiency.

Figure 4:
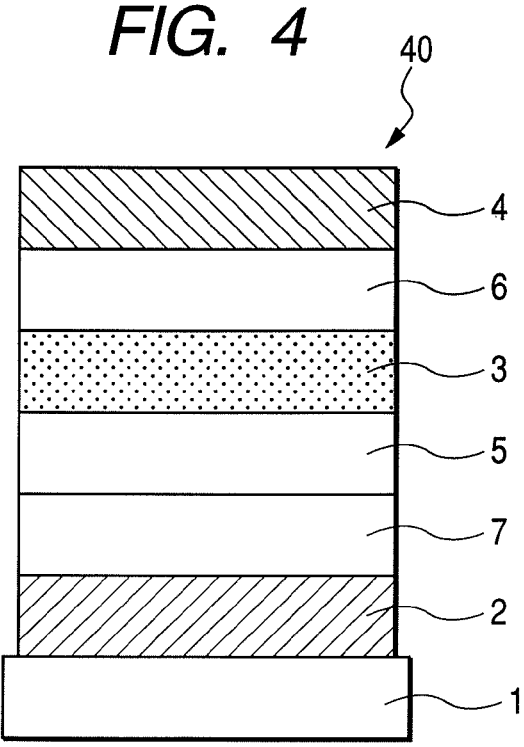
FIG. 4 is a cross sectional view illustrating an organic light-emitting device according to a fourth embodiment of the present invention.

FIG. 4 is a schematic cross-sectional view illustrating a fourth embodiment of the organic light-emitting device of the present invention. The organic light-emitting device 40 shown in FIG. 4 is different from the organic light-emitting device 30 shown in FIG. 3 in that a hole injection layer 7 is additionally provided between an anode 2 and a hole-transporting layer 5. In the organic light-emitting device 40, by additionally providing the hole injection layer 7, the adhesion between the anode 2 and the hole-transporting layer 5 or the hole injection property is improved, so that the driving voltage can be effectively reduced.

Figure 5:
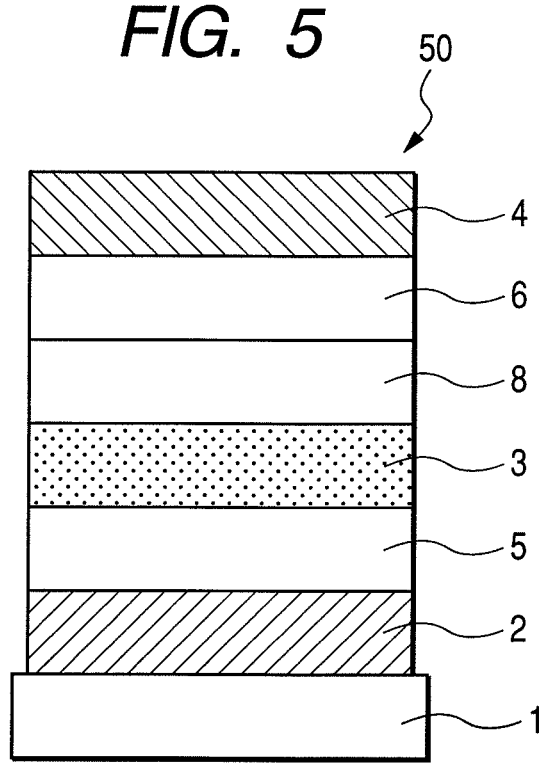
FIG. 5 is a cross sectional view illustrating an organic light-emitting device according to a fifth embodiment of the present invention.

FIG. 5 is a schematic cross-sectional view illustrating a fifth embodiment of the organic light-emitting device of the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. The configuration improves the emission efficiency of the organic light-emitting device 50 by using an organic compound with a significantly high ionization potential as the hole/exciton blocking layer 8.

FIGS. 1 to 5 merely show very basic device configurations and the configuration of the organic light-emitting device according to the present invention is not limited thereto. For example, it is possible to adopt various layer structures, such as one in which an insulating layer, an adhesive layer, or an interference layer is formed at an interface between an electrode and an organic layer. Further, a hole-transporting layer may be composed of two layers having different ionization potentials.

The organic light-emitting device according to the present invention can be used in any one of the configurations shown in FIGS. 1 to 5.

In the organic light-emitting device according to the present invention, at least one kind of the indenochrysene derivatives according to the present invention is contained in the layer including an organic compound. The term "layer including an organic compound" herein employed is intended to specifically mean the light-emitting layer 3, the hole-transporting layer 5, the electron-transporting layer 6, the hole injection layer 7, or the hole/exciton blocking layer 8 shown in FIGS. 1 to 5. The indenochrysene derivative according to the present invention is contained preferably in the light-emitting layer 3, the electron-transporting layer 6 or the hole injection layer 7, and more preferably in the light-emitting layer 3. Incidentally, the indenochrysene derivative according to the present invention may be contained either in only one layer or in a plurality of layers. Further, the indenochrysene derivative according to the present invention contained in a layer may be either a single kind or a combination of two or more kinds.

Moreover, the light-emitting layer 3 may be composed of only the indenochrysene derivative according to the present invention but is preferably composed of a host and a guest.

When a light-emitting layer is formed of a carrier transporting host and a guest, the process for light emission is composed of the following several steps.

1. Transportation of electrons/holes in the light-emitting layer
2. Generation of excitons in the host
3. Transmission of excitation energy between host molecules
4. Transfer of the excitation energy from the host to the guest The desired energy transfer and light emission in the respective steps are caused in competition with various deactivation steps.

It is needless to say that in order to increase the emission efficiency of an organic light-emitting device, the emission quantum yield of a luminescent center material itself must be large. However, how high efficiency of energy transfer between hosts or between a host and a guest can be achieved is also a large problem. In addition, the cause for degradation of light emission due to energization has not been clarified yet. However, it is assumed that the degradation is related at least to a luminescent center material itself or an environmental change of a light-emitting material due to surrounding molecules.

Therefore, when the indenochrysene derivative of the present invention is used especially as the host or the guest of the light-emitting layer, the color purity and emission efficiency of the organic light-emitting device can be improved, a high luminance can be held over a long period of time, and the energization degradation can be reduced.

As reasons for the emission degradation due to energization, in addition to the strength of the molecular skeleton in the indenochrysene derivative, the emission degradation due to the degradation in the thin film shape of the light-emitting layer, which may be occurred particularly in a case of using the derivative as a host for the light-emitting layer, is possibly mentioned. The degradation of the thin film shape is considered to be attributable to the crystallization of the organic thin film due to the temperature of a driving environment, heat generated during device driving, etc. This is, in turn, considered to be attributable to the low glass transition temperature of a material. Therefore, it is desired for the material used for the organic light-emitting device to have a high glass transition temperature. Here, since the indenochrysene derivative of the present invention has a high glass transition temperature, the durability of the organic light-emitting device can be improved.

When the indenochrysene compound of the present invention is used as a host for a light-emitting layer, the content thereof is 20 to 99.9 wt % based on the total weight of the materials constituting the light-emitting layer.

When the indenochrysene compound of the present invention is used as a guest (dopant) for a light-emitting layer, the concentration of the guest is 0.01 to 80 wt %, and preferably 1 to 40 wt % based on the weight of the host. The guest may be uniformly contained throughout the layer containing the host or may be contained in the layer so as to have a concentration gradient. Moreover, a dopant may be incorporated into only a certain region of a layer containing a host such that the layer containing the host has a region having no dopant material contained.

Meanwhile, irrespective of whether the indenochrysene derivative of the present invention is used as a host for a light-emitting layer or as a guest for the light-emitting layer, the energy gap of the host is preferably wider than that of the guest.

The organic light-emitting device of the present invention employs the indenochrysene derivative of the present invention especially as a material for constituting the light-emitting layer. Moreover, in addition to the indenochrysene derivative, a hole-transporting material, a light-emitting material, an electron-transporting material, or the like, which are hitherto known low molecular or polymer material, may be used together as needed.

Those compounds will be exemplified below.

It is preferable that the hole injecting/transporting material facilitates injection of holes from an anode and has an excellent mobility for transporting the injected holes to a light-emitting layer. As low molecular and polymer materials having hole-injection and transporting abilities include, but of course not limited to, a triarylamine derivative, a phenylenediamine derivative, a triazole derivative, an oxadiazole derivative, an imidazole derivative, a pyrazoline derivative, a pyrazolone derivative, an oxazole derivative, a fluorenone derivative, a hydrazone derivative, a stilbene derivative, a phthalocyanine derivative, a porphyrin derivative, and poly (vinylcarbazole), poly(silylene), poly(thiophen) and other conductive polymers.

As the light-emitting material other than the indenochrysene derivative of the present invention, the following compounds can be included. Specific examples of the compounds include, but of course not limited to, a fused polycyclic aromatic compound (such as a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene), a quinacridone derivative, an acridone derivative, a coumarin derivative, a pyrane derivative, Nile Red, a pyrazine derivative, a benzimidazole derivative, a benzothiazole derivative, a benzoxazole derivative, a stilbene derivative, an organometallic complex (such as an organic aluminum complex such as tris(8-quinolinolato)aluminum or an organic beryllium complex), or a polymer derivative such as a poly(phenylenevinylene) derivative, a poly(fluorene) derivative, a poly(phenylene) derivative, a poly(thienylenevinylene) derivative, or a poly(acetylene) derivative.

The electron injecting/transporting material can be arbitrarily selected from those materials which facilitate injection of electrons from a cathode and have a function of transporting the injected electrons to a light-emitting layer, and is selected in consideration of a balance with the carrier mobility of the hole-transporting material. Examples of the material having electron injecting/transporting capability include, but is not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative and an organometallic complex.

Next, the other components constituting the organic light-emitting device will be described.

An anode material used preferably has as large a work function as possible, and includes, for instance, an elemental metal such as gold, platinum, silver, copper, nickel, palladium, cobalt, selenium, vanadium and tungsten, an alloy thereof, and a metal oxide such as stannic oxide, zinc oxide, indium oxide, indium tin oxide (ITO) and indium zinc oxide. Further, a conductive polymer such as polyaniline, polypyrrole, polythiophene and polyphenylene sulfide can be employed. These electrode materials can be used singly or in combination. In addition, the anode may be either of a single layer configuration or of a multilayer configuration.

On the other hand, a cathode material used preferably has a low work function, and include, for instance, an elemental metal such as lithium, sodium, potassium, calcium, magnesium, aluminum, indium, ruthenium, titanium, manganese, yttrium, silver, lead, tin, and chromium. Alternatively, an alloy made of a plurality of the above metals, such as lithium-indium, sodium-potassium, magnesium-silver, aluminum-lithium, aluminum-magnesium, and magnesium-indium can also be used. A metal oxide such as indium tin oxide (ITO) can be also used. These electrode materials can be used singly or in combination. In addition, the cathode may be either of a single layer configuration or of a multilayer configuration.

A substrate used in the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflection film to thereby control the emission color.

Incidentally, after a device has been produced, a protective layer or an encapsulation layer may further be provided, for the purpose of preventing contact with oxygen or moisture.

Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a photocurable resin. Further, the produced device may also be covered with glass, a gas-impermeable film and a metal, or be packaged with a suitable encapsulation resin.

In addition, in the organic light-emitting device of the present invention, it is also possible to provide a thin film transistor (TFT) on the substrate and form a device by connecting thereto.

Further, as to the direction in which light is taken out of the device, any one of a bottom emission configuration (configuration in which light is taken out from a substrate side) and a top emission configuration (configuration in which light is taken out from a side opposite to the substrate side) may be adopted as needed.

In the organic light-emitting device of the present invention, a layer containing the indenochrysene compound of the present invention and other layers composed of an inorganic compound are formed by the below-mentioned methods. Generally, a thin film is formed by use of a vacuum evaporation method, an ion plating method, a sputtering method, or a plasma CVD method. In particular, since a layer formed by the vacuum evaporation method or a solution coating method is less susceptible to crystallization or the like and is excellent in stability over time, such a layer is preferable. Further, a thin film may be formed by use of a known coating method of applying an organic compound dissolved in a suitable solvent (such as spin coating, dipping, casting, LB method, ink jet method). Particularly, when a film is formed through the coating method, the film can be formed by additionally using a suitable binder resin.

The above described binder resin can be selected from a wide range of binding resins, and includes, for instance, polyvinylcarbazole resin, polycarbonate resin, polyester resin, polyarylate resin, polystyrene resin, ABS resin, polybutadiene resin, polyurethane resin, acrylic resin, methacrylic resin, butyral resin, polyvinylacetal resin, polyamide resin, polyimide resin, polyethylene resin, polyether sulfonic resin, diallylphthalate resin, phenolic resin, epoxy resin, silicone resin, polysulfonic resin and urea resin, but is not limited to them. In addition, the binder resin may be singly used, or be used in combination as a copolymer. Furthermore, an additive such as a known plasticizer, antioxidant, and ultraviolet absorber may be further used, as needed.

EXAMPLES

Hereinafter, the present invention will be specifically described by way of examples, but the present invention is not limited thereto.

Example 1

Production Method of Exemplified Compound No. 306

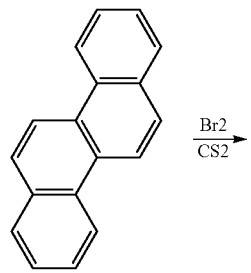

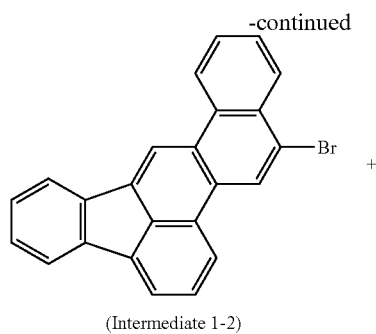

(Intermediate 1-2)

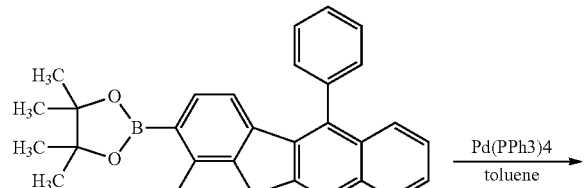

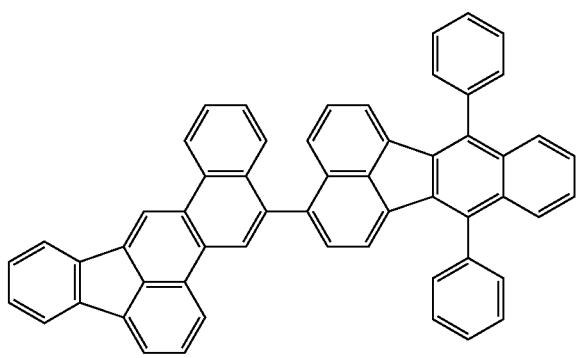

Exemplified Compound No. 306

(1) Synthesis of Intermediate 1-1 (indeno[1,2,3-hi]chrysene)

First, Intermediate 1-1 (indeno[1,2,3-hi]chrysene) was obtained by using chrysene as a starting material with reference to Journal of Organic Chemistry 1987, 52, 5668.

(2) Synthesis of Intermediate 1-2 (5-bromoindeno[1,2,3-hi]chrysene)

Next, Intermediate 1-2 (5-bromoindeno[1,2,3-hi]chrysene) was obtained by using Intermediate 1-1 (indeno[1,2,3-hi]chrysene) obtained in (1) above as a starting material with reference to the synthesis method described in Journal of American Chemical Society 1989, 111, 3809.

(3) Synthesis of Exemplified Compound No. 306

The following reagents and solvents were charged in a reaction vessel under nitrogen atmosphere, and a reaction solution was suspended.

Intermediate 1-2: 93 mg (0.24 mmol)
2-(7,12-diphenylbenzo[k]fluoranthene-3-yl)-4,4,5,5-tetramethyl-1,3,2-dioxaborolan: 142 mg (0.27 mmol)
tetrakistriphenylphosphin palladium: 14 mg (0.01 mmol)
Toluene: 20 ml
Ethanol: 10 ml
10% sodium carbonate solution: 8 ml Next, the reaction solution was stirred for 3 hours under heating and reflux. After that, the reaction solution was cooled to room temperature, and water was added to terminate the reaction. An organic layer was separated by a separation operation, and was then washed with water twice. Next, the residue obtained by removing the solvent by distillation under reduced pressure was purified by silica gel column chromatography (using a mixture of toluene and heptane at a ratio of 1:1 as a developing solvent), whereby 124 mg of Exemplified Compound No. 306 were obtained.

Then, 704.2 as M+ of the compound was confirmed by Matrix Assisted Laser Desorption/Ionization—Time of Flight Mass Spectrometry (MALDI-TOFMS).

The structure of the compound was identified by NMR measurement. The assignment of peaks is shown below.

$^1$H-NMR (CDCl$_3$): δ (ppm)=9.31 (s, 1H), 9.04 (d, 1H, J=8.69 Hz), 8.68 (s, 1H), 8.43 (d, 1H, J=8.23 Hz), 8.17-8.15 (m, 1H), 8.02 (d, 1H, J=6.86 Hz), 7.98-7.96 (m, 1H), 7.77-7.60 (m, 15H), 7.52-7.42 (m, 5H), 7.35 (d, 1H, J=8.23 Hz), 7.17 (d, 2H, J1=8.46 Hz, J2=7.09), 6.78 (d, 1H, J=7.32 Hz), 6.63 (d, 1H, J=6.40)

Figure 6:
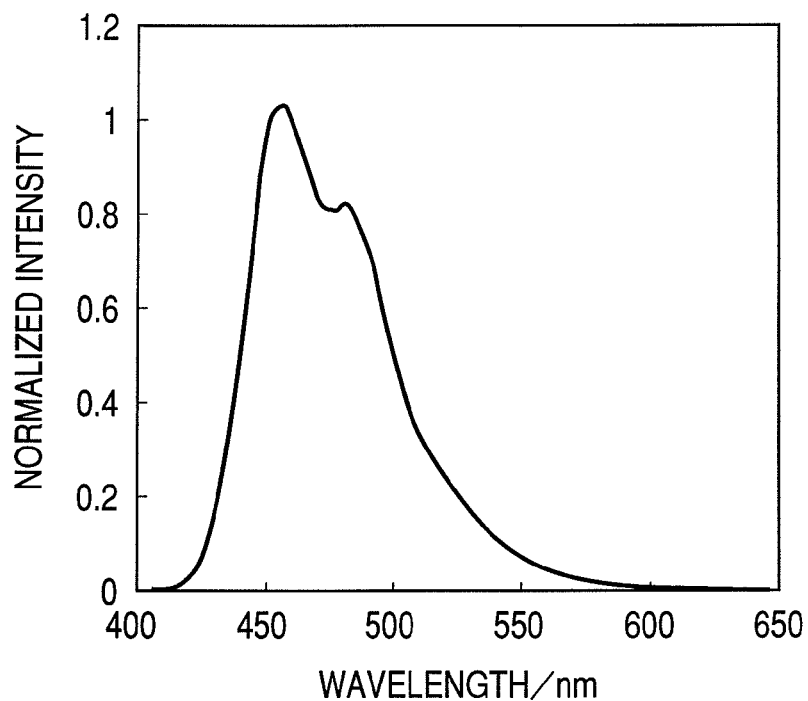
FIG. 6 is a graphical representation showing a PL spectrum of a toluene solution ($1.0\times10^{-5}$ mol/L) of Exemplified Compound 306.

An emission spectrum (PL spectrum) in a toluene solution ($1.0\times10^{-5}$ mol/L) of Exemplified Compound No. 306 was measured. As a result, a PL spectrum shown in FIG. 6 was obtained. The PL spectrum was a blue emission spectrum having an emission peak at 454 nm and a full width at half maximum of 62 nm.

Exemplified Compound No. 306 was evaluated for its quantum yield by the following method.

First, a toluene solution having a concentration of $10^{-6}$ mol/l was prepared, and the absorbance of the solution at a wavelength of 345 nm was measured with a spectrophotometer (U-3310 (trade name); manufactured by Hitachi, Ltd.). Next, the emission spectrum of the solution with an excitation wavelength of 345 nm was measured with a fluorescence spectrophotometer (F-4500 (trade name); manufactured by Hitachi, Ltd.). A relative value for the emission quantum yield of the compound with a value for diphenylanthracene being defined as 0.95 was determined based on the peak area of the emission spectrum and the absorbance. Table 2 shows the result.

Moreover, the following compounds are each used in place of the 2-(7,12-diphenylbenzo[k]fluoranthene-3-yl)-4,4,5,5-tetramethyl-1,3,2-dioxaborolan which was used in (2) of Example 1. Exemplified Compounds shown below can be synthesized by following the same procedure as in Example 1 except the above.

(Example Compound 101): biphenyl-4-yl-boronic acid
(Example Compound 201): naphthalene-2-yl-boronic acid
(Example Compound 207): naphthalene-1-yl-boronic acid
(Example Compound 215): 2-(9,9-dimethyl-9H-fluorene-2-yl)-4,4,5,5-tetramethyl-1,3,2-dioxaborolan
(Example Compound 228): 4,4,5,5-tetramethyl2-yl-(9,9,9',9'-tetramethyl-9H-9H'-2,2'-bifluorene-7-yl)-1,3,2-dioxaborolan
(Example Compound 301): 2-(fluoranthene-3-yl)-4,4,5,5-tetramethyl-1,3,2-dioxaborolan
(Example Compound 317): 4,4,5,5-tetramethyl-2-(pyrene-1-yl)-1,3,2-dioxaborolan
(Example Compound 321): 2-(benzo[C]phenanthrene-4-yl)-4,4,5,5-tetramethyl-1,3,2-dioxaborolan

Example 2

Production Method of Exemplified Compound No. 607

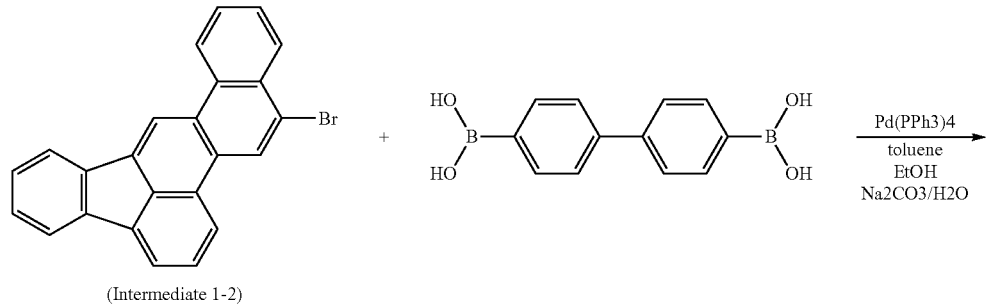

(Intermediate 1-2)

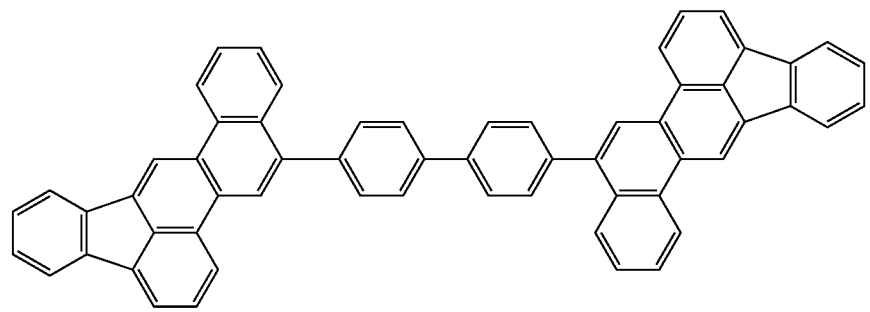

Exemplified Compound No. 607

The following reagents and solvents were charged in a reaction vessel under nitrogen atmosphere, and a reaction solution was suspended.
Intermediate 1-2: 305 mg (0.80 mmol)
Biphenyl-4,4'-diboronic acid: 92 mg (0.38 mmol)
Tetrakistriphenylphosphin palladium: 44 mg (0.04 mmol)
Toluene: 9 ml
Ethanol: 9 ml
10% sodium carbonate solution: 6 ml Next, the reaction solution was stirred for 3 hours under heating and reflux. After that, the reaction solution was cooled to room temperature, and water was added to terminate the reaction. Next, the solution was filtrated, and the resultant solid was purified by alumina column chromatography (developing solvent: chlorobenzene). After that, the purified product was further subjected to slurry washing with chlorobenzene, and was filtered off, whereby 200 mg of Exemplified Compound No. 607 were obtained.

Then, 754.2 as M+ of the compound was confirmed by Matrix Assisted Laser Desorption/Ionization—Time of Flight Mass Spectrometry (MALDI-TOFMS).

Figure 7:
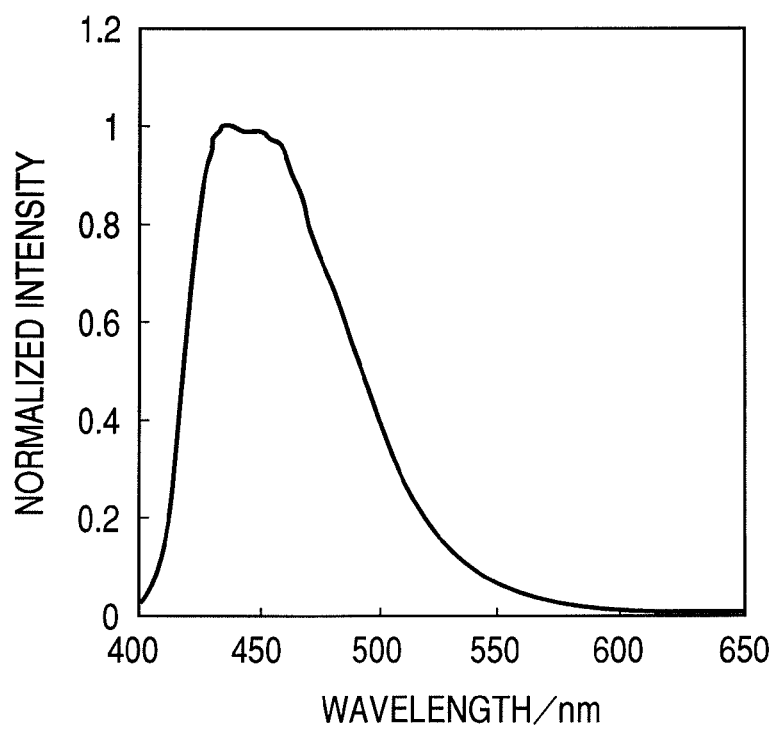
FIG. 7 is a graphical representation showing a PL spectrum of a toluene solution ($1.0\times10^{-5}$ mol/L) of Exemplified Compound 607.

A PL spectrum in a toluene solution ($1.0 \times 10^{-5}$ mol/L) of Exemplified Compound No. 607 was measured. As a result, a PL spectrum shown in FIG. 7 was obtained. The PL spectrum was a blue emission spectrum having an emission peak at 441 nm and a full width at half maximum of 74 nm.

Exemplified Compound No. 607 was evaluated for its quantum yield in the same manner as in Example 1. Table 2 shows the result.

In addition, the following exemplified compounds can each be synthesized by following the same procedure as in Example 2 with the exception that the following compounds are each used instead of biphenyl-4,4'-diborolanic acid in Example 2.

(Example Compound 601): 1,4-phenyl diboronic acid
(Example Compound 605): 1,3-phenyl diboronic acid
(Example Compound 612): biphenyl-3,4'-diboronic acid
(Example Compound 617): benzene-1,3,5-tolyltriboronic acid

Example 3

Production Method of Exemplified Compound No. 309

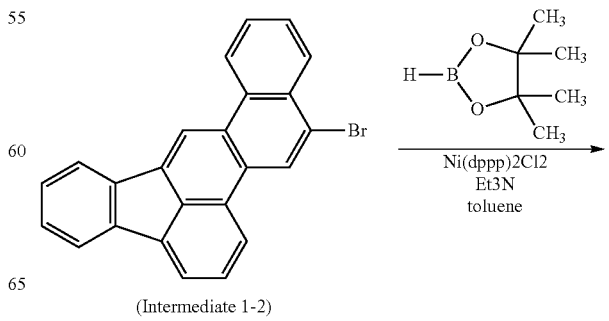

(Intermediate 1-2)

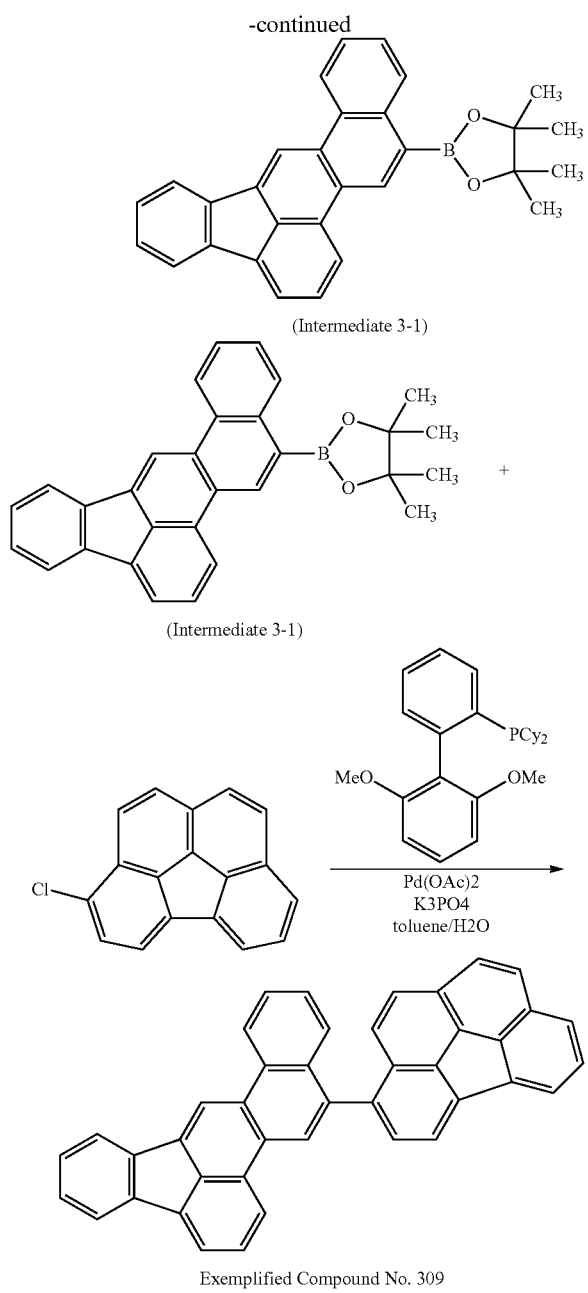

(Intermediate 3-1)

(Intermediate 3-1)

Exemplified Compound No. 309

(1) Synthesis of Intermediate 3-1 (2-(indeno[1,2,3-hi]chrysen-5-yl)-4,4,5,5-tetramethyl-1,3,2-dioxaborolane)

The following reagent and solvent were charged in a 100-mL reaction vessel.
  Intermediate 1-2: 1.0 g (2.62 mmol)
  Bis(diphenylphosphinopropane)dichloronickel: 0.57 g (1.05 mmol)

Next, the inside of the reaction vessel was purged with nitrogen. After the nitrogen purging had been repeated ten times, the following reagent and solvents were sequentially charged in the reaction vessel under nitrogen flow.
  Toluene: 50 mL
  Triethylamine: 0.8 g (7.87 mmol)
  4,4,5,5-tetramethyl-1,3,2-dioxaborolane: 1.0 g (7.87 mmol)

Next, the temperature of a bath was increased to 100° C., and the reaction solution was heated with stirring at that temperature for 4.5 hours. After that, the solution was allowed to be cooled to room temperature, and water was added at 10° C. or lower to terminate the reaction. Next, chloroform was added to the resultant, and an organic layer was separated by a separation operation and washed with a saturated brine three times and with water once. After that, the solvent was evaporated under reduced pressure. A mixed solvent of toluene and methanol was added to the resultant residue, and the solvent was evaporated again to perform crystallization. Chlorobenzene and methanol were added to the resultant coarse crystal and recrystallization was performed, whereby 670 mg of Intermediate 3-1 as a white solid was obtained.

(2) Synthesis of Exemplified Compound No. 309

The following reagents and solvents were charged in a reaction vessel under nitrogen atmosphere.
  Intermediate 3-1: 200 mg (0.47 mmol)
  5-chlorobenzo[ghi]fluoranthene: 146 mg (0.56 mmol)
  Dicyclohexyl(2',6'-dimethoxybiphenyl-2-yl)phosphin: 7.7 mg (0.02 mmol)
  Tripotassium phosphate: 198 mg (0.93 mmol)
  Toluene: 20 ml
  Water: 2 ml
  Palladium acetate: 2.1 mg (0.01 mmol)

Next, the reaction solution was stirred for 2 hours under heating and reflux. After that, the reaction solution was cooled to room temperature, and water was added to terminate the reaction. Next, toluene was added to the resultant, and an organic layer was separated by a separation operation and then washed with water twice. Next, the residue obtained by evaporating the solvent under reduced pressure was purified by column chromatography (silica gel: 200 g, mobile phase: toluene/heptane=1/3). Next, the purified product was subjected to slurry washing with a mixed solvent of toluene and methanol, whereby 80 mg of Exemplified Compound No. 309 as a pale yellow crystal were obtained.

Then, 526.1 as M+ of the compound was confirmed by Matrix Assisted Laser Desorption/Ionization—Time of Flight Mass Spectrometry (MALDI-TOFMS).

The structure of the compound was identified by NMR measurement. The assignment of peaks is shown below.

$^1$H-NMR (CDCl$_3$): δ (ppm)=8.20 (d, 1H, J=7.32 Hz), 8.16 (d, 1H, J=6.86 Hz), 7.99 (d, 1H, J=8.69 Hz), 7.95 (d, 1H, J=8.23 Hz), 7.90 (d, 1H, J=8.69 Hz), 7.78 (d, 1H, J=8.69 Hz), 7.73-7.59 (m, 17H), 7.51 (d, 1H, J=7.32 Hz), 7.44-7.40 (m, 2H), 6.77 (d, 1H, J=7.32 Hz), 6.65 (d, 1H, J=6.86)

Figure 8:
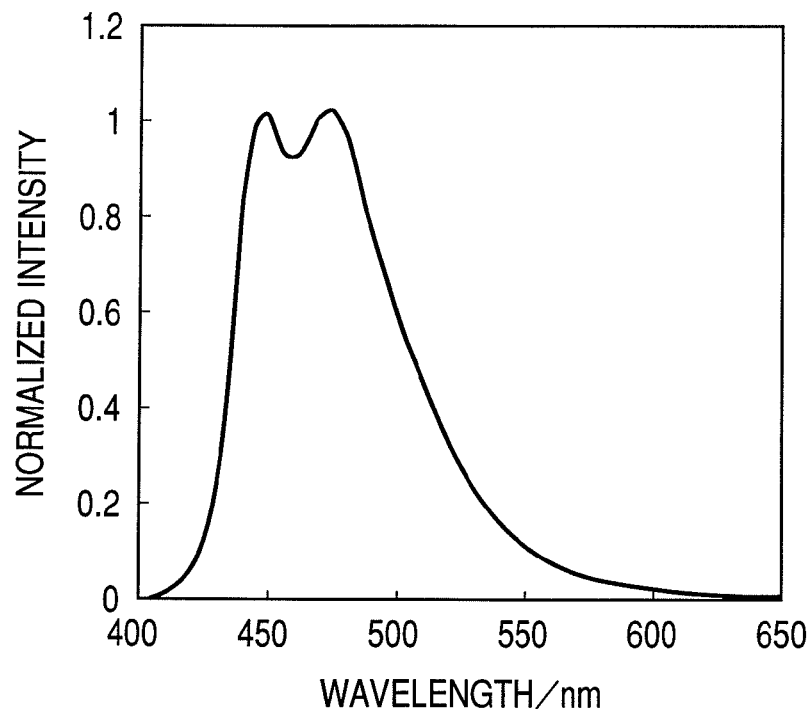
FIG. 8 is a graphical representation showing a PL spectrum of a toluene solution ($1.0\times10^{-5}$ mol/L) of Exemplified Compound 309.

A PL spectrum in a toluene solution (1.0×10$^{-5}$ mol/L) of Exemplified Compound No. 309 was measured. As a result, a PL spectrum shown in FIG. 8 was obtained. The PL spectrum was a blue emission spectrum having an emission peak at 450 nm and a full width at half maximum of 71 nm. Exemplified Compound No. 309 was evaluated for its quantum yield in the same manner as in Example 1. Table 2 shows the result.

In addition, the following exemplified compounds can each be synthesized by following the same procedure as in (2) of Example 3 with the exception that the following compounds are each used instead of 5-chlorobenzo[ghi]fluoranthene in Example 2.

(Example Compound No. 325): 5-bromoindeno[1,2,3-hi]chrysene
(Example Compound No. 401): 2-chloroquinoline
(Example Compound No. 404): 3-chloroquinoline
(Example Compound No. 406): 6-chloroquinoline
(Example Compound No. 408): 7-chloroquinoline
(Example Compound No. 410): 4-chloroquinoline
(Example Compound No. 412): 5-chloroquinoline (Example Compound No. 414): 8-chloroquinoline
(Example Compound No. 417): 1-chloroisoquinolin
(Example Compound No. 419): 4-chloroisoquinolin
(Example Compound No. 421): 8-chloroisoquinolin
(Example Compound No. 423): 3-chloroisoquinolin
(Example Compound No. 425): 6-chloroisoquinolin
(Example Compound No. 427): 7-chloroisoquinolin
(Example Compound No. 429): 2-chloro-5,5'-dimethyl-5H-indeno[1,2-b]pyridine
(Example Compound No. 431): 4-chloro-5,5'-dimethyl-5H-indeno[1,2-b]pyridine
(Example Compound No. 433): 8-bromo-5,5'-dimethyl-5H-indeno[1,2-b]pyridine
(Example Compound No. 435): 7-bromo-5,5'-dimethyl-5H-indeno[1,2-b]pyridine
(Example Compound No. 501): 2-chloroindeno[1,2,3-de]quinoline
(Example Compound No. 519): 3-bromo-7,12-diphenylacenaphto[1,2-g]isoquinoline
(Example Compound No. 520): 4-bromo-7,12-diphenylacenaphto[1,2-g]isoquinoline Comparative Example 1

Compound A-0 shown below was evaluated for its quantum yield in the same manner as in Example 1. Table 2 shows the result.

TABLE 2

Compound A-0

| Sample | | Relative quantum yield |
|---|---|---|
| Example 1 | Exemplified Compound No. 306 | 0.85 |
| Example 2 | Exemplified Compound No. 607 | 0.73 |
| Example 3 | Exemplified Compound No. 309 | 0.58 |
| Comparative Example 1 | Compound A-0 | 0.39 |

As shown in Table 1, the indenochrysene derivative of the present invention has a higher quantum yield than that of indenochrysene having no substituent (Compound A-0). Accordingly, it was seen that the introduction of a skeleton structure having a higher quantum yield than that of an indenochrysene skeleton as a substituent into the indenochrysene skeleton was able to improve the quantum yield of the skeleton significantly.

In addition, in Example 3, a substituent having a lower quantum yield than that of the indenochrysene skeleton (benzo[ghi]fluoranthene) is introduced as a substituent. Even in this case, however, a substituent allowing the formation of a bond constitution between peri-position and peri-position is introduced. It was seen that the substituent was able to improve the quantum yield of the indenochrysene derivative.

Example 4

Production Method of Exemplified Compound No. 701

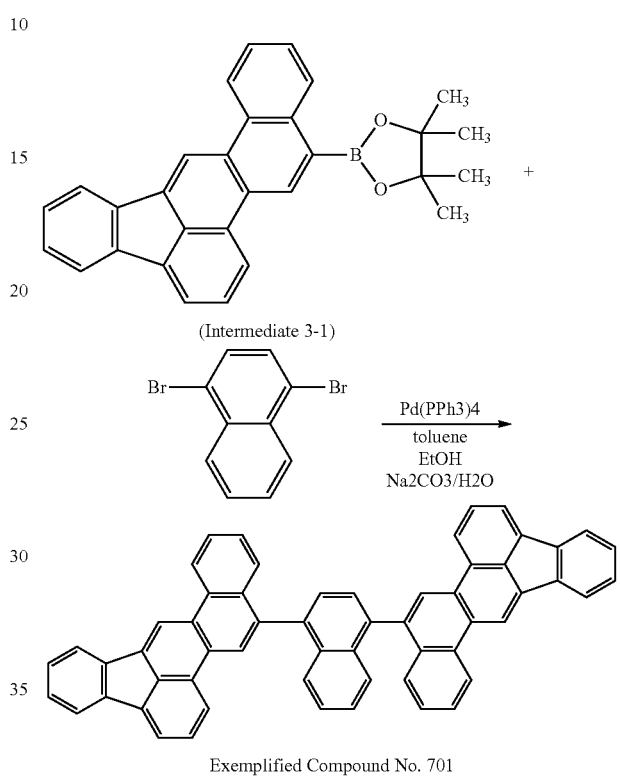

(Intermediate 3-1)

Exemplified Compound No. 701

The following reagents and solvents were charged in a reaction vessel under nitrogen atmosphere, and a reaction solution was suspended.
Intermediate 3-1: 277 mg (0.65 mmol)
1,4-dibromonaphthalene: 88 mg (0.34 mmol)
Tetrakistriphenylphosphin palladium: 36 mg (0.03 mmol)
Toluene: 30 ml
Ethanol: 15 ml
10% sodium carbonate: 12 ml Next, the reaction solution was stirred for 2 hours under heating and reflux. After that, the reaction solution was cooled to room temperature, and water was added to terminate the reaction. Next, an organic layer was separated by a separation operation, and was then washed with water twice. After that, the residue obtained by evaporating the solvent under reduced pressure was purified by alumina column chromatography (using a mixture of chlorobenzene and ethyl acetate at a ratio of 1:1 as a developing solvent). Next, the purified product was subjected to slurry washing with a mixed liquid of methanol and toluene, and was filtered off, whereby 149 mg of Exemplified Compound No. 701 as a white crystal was obtained.

Then, 728.2 as M+ of the compound was confirmed by Matrix Assisted Laser Desorption/Ionization—Time of Flight Mass Spectrometry (MALDI-TOFMS).

The structure of Exemplified Compound No. 701 was identified by NMR measurement. The assignment of peaks is shown below.

$^1$H-NMR (CDCl$_3$): δ (ppm)=9.40 (s, 2H), 9.13 (dd, 2H, J1=8.46 Hz, J2=1.14), 8.93 (s, 1H), 8.89 (s, 1H), 8.62 (d, 1H, J=7.59 Hz), 8.57 (d, 1H, J=8.39 Hz), 8.23-8.20 (m, 2H), 8.08 (d, 2H, J=6.86 Hz), 8.02-8.00 (m, 2H), 7.86-7.81 (m, 8H), 7.67 (dd, 2H, J1=6.40 Hz, J2=3.20), 7.63-7.57 (m, 2H), 7.54-7.47 (m, 4H), 7.32 (dd, 2H, J1=6.40 Hz, J2=3.20)

Figure 9:
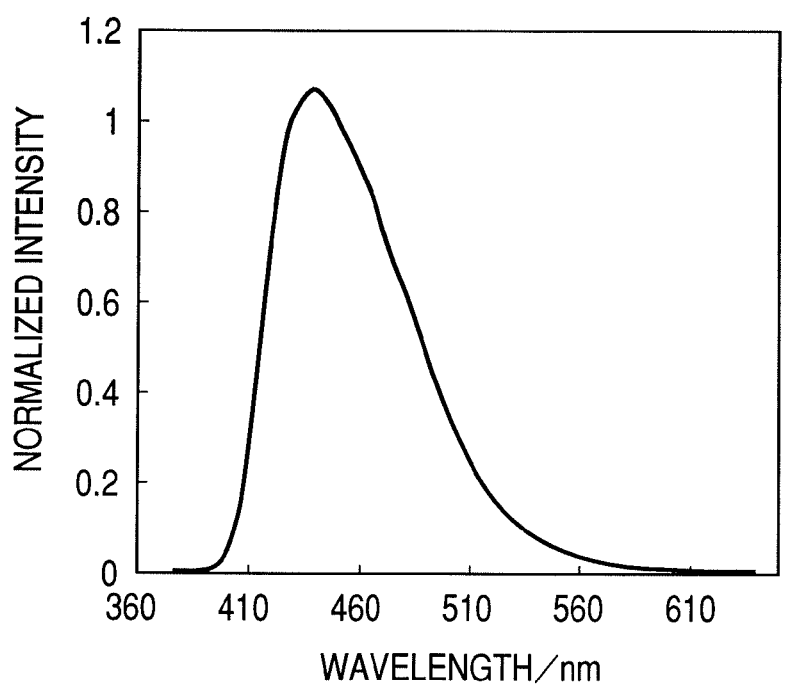
FIG. 9 is a graphical representation showing a PL spectrum of a toluene solution ($1.0\times10^{-5}$ mol/L) of Exemplified Compound 701.

A PL spectrum in a toluene solution (1.0×10$^{-5}$ mol/L) of Exemplified Compound No. 701 was measured. As a result, a PL spectrum shown in FIG. 9 was obtained. The PL spectrum was a blue emission spectrum having an emission peak at 438 nm and a full width at half maximum of 70 nm.

In addition, the following exemplified compounds can each be synthesized by following the same procedure as in Example 4 with the exception that the following compounds are each used instead of 1,4-dibromonaphthalene in Example 4.
(Example Compound 704): 1,5-dibromonapthalene
(Example Compound 707): 2,7-dibromonaphthalene
(Example Compound 713): 2-bromo-7-iodo-9,9-dimethyl-9H-fluorene
(Example Compound 716): 7,7'-dibromo-9,9,9',9'-tetramethyl-9H-9H'-2,2'-bifluorene
(Example Compound 719): 9,10-dibromoanthracene
(Example Compound 722): 6,12-dibromochrysene Example 5

An organic light-emitting device having a structure shown in FIG. 4 was produced by the following method.

On a glass substrate (substrate 1), indium tin oxide (ITO) was formed into a film in a thickness of 120 nm as an anode 2 by a sputtering method. Next, the glass substrate having the ITO film formed thereon was ultrasonically cleaned sequentially with acetone and isopropyl alcohol (IPA), subsequently cleaned with pure water, dried, and further cleaned with UV/ozone. The glass substrate thus treated was used as a transparent conductive support substrate.

Next, a solution of Compound A1 represented by the following formula as a hole injection material in chloroform at a concentration of 0.1 wt % was prepared.

Compound A1

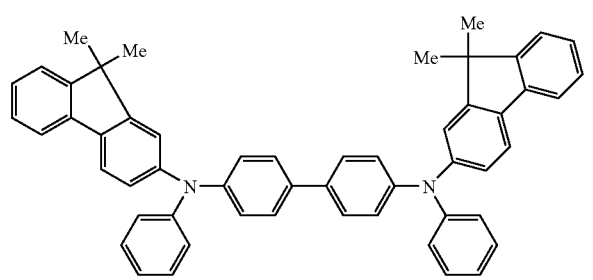

The solution was dropped onto the ITO electrode. After the dropping, the substrate was subjected to spin coating by being rotated initially at 500 RPM for 10 seconds and then at 1,000 RPM for 40 seconds, whereby a film was formed. After that, the film was dried in a vacuum oven at 80° C. for 10 minutes so that the solvent in the film was completely removed, whereby a hole injection layer 7 was formed.

Next, on the hole injection layer 7, Compound A2 represented by the following formula was deposited into a film in a thickness of 15 nm by a vacuum evaporation method to form a hole-transporting layer 5 under the conditions of a degree of vacuum during evaporation of 1.0×10$^{-4}$ Pa and a film formation rate of 0.1 to 0.2 nm/sec.

Compound A2

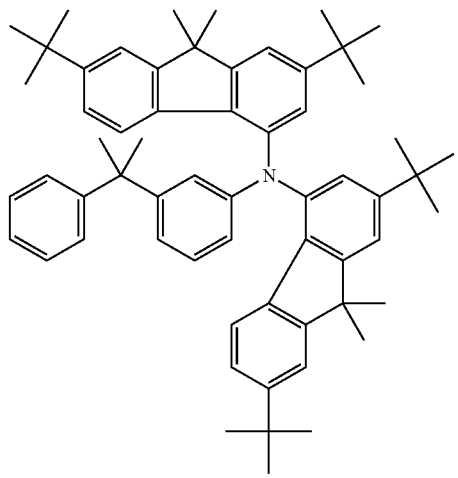

Then, on the hole-transporting layer 5, Compound A3 as a host represented by the following formula and Exemplified Compound No. 306 as a guest were coevaporated at a weight ratio of 98:2 in a thickness of 30 nm to provide a light-emitting layer 3. At this time, the light-emitting layer 3 was formed under the conditions of a degree of vacuum during evaporation of 1.0×10$^{-4}$ Pa and a film formation rate of 0.1 to 0.2 nm/sec.

Compound A3

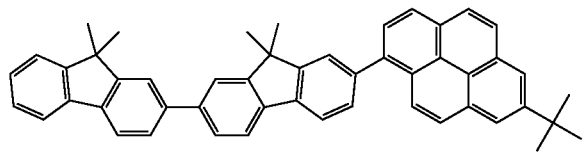

Further, on the light-emitting layer 3, a film of 2,9-bis[2-(9,9'-dimethylfluorenyl)]-1,10-phenanthroline was deposited in a thickness of 30 nm by a vacuum evaporation method to form an electron-transporting layer 6. At this time, the electron-transporting layer 6 was formed under the conditions of a degree of vacuum during evaporation of 1.0×10$^{-4}$ Pa and a film formation rate of 0.1 to 0.2 nm/sec.

Next, on the electron-transporting layer 6, a film of lithium fluoride (LiF) was deposited in a thickness of 0.5 nm by a vacuum evaporation method under the conditions of a degree of vacuum during evaporation of 1.0×10$^{-4}$ Pa and a film formation rate of 0.01 nm/sec. Then, on the LiF film, an aluminium film having a thickness of 100 nm was formed by a vacuum evaporation method under the conditions of a degree of vacuum during evaporation of 1.0×10$^{-4}$ Pa and a film formation rate of 0.5 to 1.0 nm/sec. Here, the lithium fluoride film and the aluminium film function as an electron ejection electrode (cathode 4).

The resultant organic light-emitting device was covered with a protective glass plate in a dry air atmosphere so that the device was not degraded through adsorbing moisture, and was encapsulated with an acrylic resin adhesive. As described above, the organic light-emitting device was obtained.

For the thus obtained device, the device characteristics were evaluated. Specifically, a voltage of 4.3 V was applied to the device with the ITO electrode (anode 2) being connected to a positive electrode of a power supply and the Al electrode (cathode 4) being connected to a negative electrode of the power supply. As a result, the device was observed to emit blue light with an emission efficiency of 7.3 cd/A. In addition, the device was observed to emit blue light with CIE chromaticity coordinates of x=0.15 and y=0.16.

Further, when a voltage was applied to the device in a nitrogen atmosphere while keeping a current density of 100 mA/cm$^2$ for 100 hours, an initial luminance of 6,307 cd/m$^2$ was reduced to 5,135 cd/m$^2$ after passage of the 100 hours, which showed small luminance degradation.

Example 6

A device was produced by following the same procedure as in Example 5 with the exception that Exemplified Compound No. 309 was used instead of Exemplified Compound No. 306 used as the guest for the light-emitting layer 3 in Example 5 and the thin film of the light-emitting layer 3 was formed by performing coevaporation such that the weight ratio of host to guest was 95:5.

The characteristics of the thus obtained device was evaluated in the same manner as in Example 5. As a result, when a voltage of 4.3 V was applied, the device was observed to emit light with a current efficiency of 6.1 cd/A. In addition, the device was observed to emit blue light with CIE chromaticity coordinates of x=0.16 and y=0.23.

Further, when a voltage was applied to the device in a nitrogen atmosphere while keeping a current density of 100 mA/cm$^2$ for 100 hours, an initial luminance of 5,527 cd/m$^2$ was reduced to 4,675 cd/m$^2$ after passage of the 100 hours, which showed small luminance degradation.

Example 7

A device was produced by following the same procedure as in Example 5 with the exception that Exemplified Compound No. 701 was used instead of Exemplified Compound No. 306 used as the guest for the light-emitting layer 3 in Example 5, Compound A4 shown below was used instead of Compound A3 used as the host for the light-emitting layer 3 in Example 5, and the thin film of the light-emitting layer 3 was formed by performing coevaporation such that the weight ratio of host to guest was 95:5.

The characteristics of the thus obtained device was evaluated in the same manner as in Example 5. As a result, when a voltage of 4.3 V was applied, the device was observed to emit light with a current efficiency of 5.1 cd/A. In addition, the device was observed to emit blue light with CIE chromaticity coordinates of x=0.16 and y=0.14.

Further, when a voltage was applied to the device in a nitrogen atmosphere while keeping a current density of 100 mA/cm$^2$ for 100 hours, an initial luminance of 4,341 cd/m$^2$ was reduced to 3,300 cd/m$^2$ after passage of the 100 hours, which showed small luminance degradation.

As described above, the organic light-emitting device containing the indenochrysene derivative of the present invention can emit light with a high luminance at a low applied voltage, and is excellent in durability. In particular, the organic light-emitting device using the indenochrysene derivative as a guest for its light-emitting layer serves as an excellent organic light-emitting device that emits blue light. That is, it was shown that appropriate molecular modification allowed the device to show a blue emission hue having an emission peak at 430 nm or more and 470 nm or less. Moreover, it was also shown that the device was able to emit light with a high luminance at a low applied voltage, and was excellent in durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-140749, filed May 28, 2007, which is hereby incorporated by reference herein in its entirety.

The invention claimed is:

1. An indenochrysene derivative represented by the general formula (1):

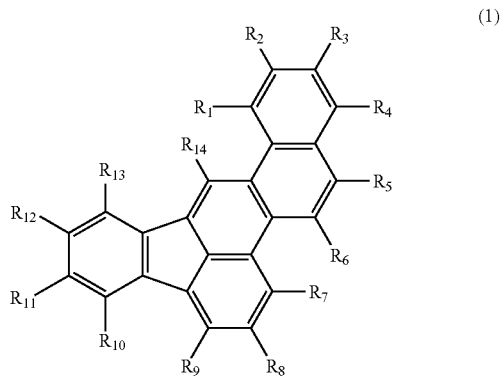

(1)

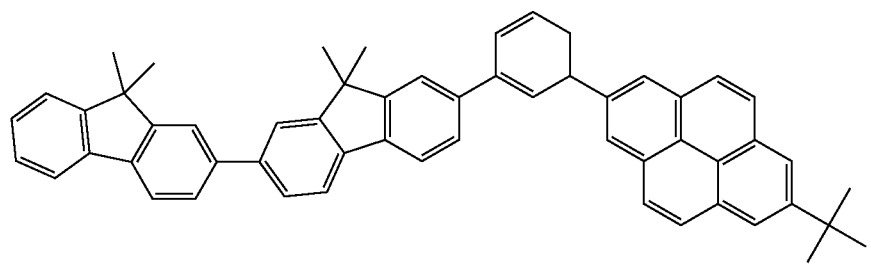

Compound A4 wherein $R_5$ represents a group which is selected from the group consisting of a benzo[k]fluoranthenyl group and a benzo[ghi]fluoranthenyl group and may be substituted with a substituent selected from the group consisting of a methyl group, an ethyl group, a propyl group, a tert-butyl group, a phenyl group and a biphenyl group;

wherein $R_1$, $R_2$, $R_4$, $R_6$, $R_7$, $R_8$, $R_{11}$, $R_{13}$, and $R_{14}$ each represent a hydrogen atom;

wherein $R_3$ and $R_9$ each represent, independently of one another, a hydrogen atom, a methyl group or a phenyl group; and wherein $R_{10}$ and $R_{12}$ each represent, independently of one another, a hydrogen atom or a methyl group.

2. An indenochrysene derivative represented by one of the following formulae:

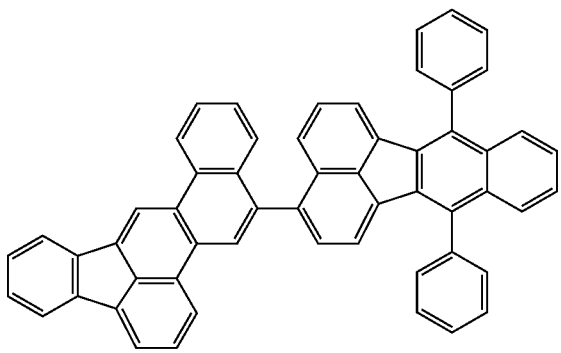

or

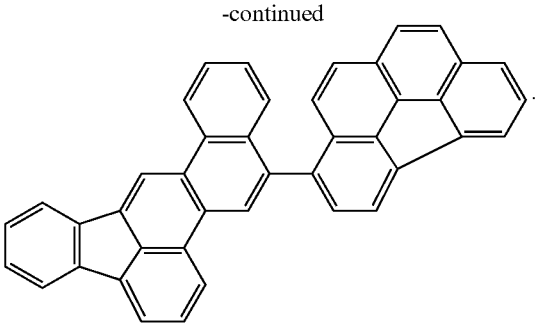

3. An organic light-emitting device comprising:
an anode and a cathode; and
a layer comprising an organic compound interposed between the anode and the cathode,
wherein either one of the anode and the cathode is formed of a transparent or translucent electrode material, and
wherein the layer comprises at least one of the indenochrysene derivatives set forth in claim 1.

4. The organic light-emitting device according to claim 3, wherein the indenochrysene derivative is contained in a light-emitting layer.

5. The organic light-emitting device according to claim 4, wherein the light-emitting layer comprises a host and a guest.

6. An apparatus comprising a substrate and the organic light-emitting device set forth in claim 3, wherein the apparatus further comprises a TFT connected to the organic light-emitting device.

7. An apparatus comprising a substrate and the organic light-emitting device set forth in claim 3, wherein light emitted by the organic light-emitting device is extracted from the substrate side.

8. An apparatus comprising a substrate and the organic light-emitting device set forth in claim 3, wherein light emitted by the organic light-emitting device is extracted from a side opposite to the substrate side.

* * * * *